(12) United States Patent
Tsamir et al.

(10) Patent No.: US 10,111,683 B2
(45) Date of Patent: Oct. 30, 2018

(54) POSITIONING AND TISSUE SENSING DEVICES AND METHODS

(71) Applicant: OMEQ MEDICAL LTD., M.P. Misgav (IL)

(72) Inventors: Oded Tsamir, Tel Aviv (IL); Lior Margalit, Herzlia (IL)

(73) Assignee: OMEQ MEDICAL LTD., M.P. Misgav (IL)

( * ) Notice: Subject to any disclaimer, the term of this patent is extended or adjusted under 35 U.S.C. 154(b) by 178 days.

(21) Appl. No.: 14/653,354

(22) PCT Filed: Dec. 22, 2013

(86) PCT No.: PCT/IL2013/051047
§ 371 (c)(1),
(2) Date: Jun. 18, 2015

(87) PCT Pub. No.: WO2014/097301
PCT Pub. Date: Jun. 26, 2014

(65) Prior Publication Data
US 2015/0342635 A1    Dec. 3, 2015

Related U.S. Application Data

(60) Provisional application No. 61/745,561, filed on Dec. 22, 2012.

(51) Int. Cl.
*A61B 17/34* (2006.01)
*A61M 25/01* (2006.01)
(Continued)

(52) U.S. Cl.
CPC ...... *A61B 17/3403* (2013.01); *A61B 17/3401* (2013.01); *A61B 17/3417* (2013.01);
(Continued)

(58) Field of Classification Search
CPC .. A61M 2025/0003; A61M 2025/0007; A61M 2025/0018; A61M 2025/0166;
(Continued)

(56) References Cited

U.S. PATENT DOCUMENTS 4,940,458 A    7/1990  Cohn
2010/0069851 A1*  3/2010  Vad ............... A61B 17/3401
                                               604/240

(Continued)

FOREIGN PATENT DOCUMENTS

WO    WO 2011/158227    12/2011

OTHER PUBLICATIONS

International Search Report of International Application No. PCT/IL2013/051047 dated Apr. 2, 2015.

*Primary Examiner* — Quynh-Nhu H Vu
(74) *Attorney, Agent, or Firm* — Pearl Cohen Zedek Latzer Baratz LLP

(57) ABSTRACT

A positioning device with sensing capacities is provided, which facilitates needle or catheter introduction into a body tissue or cavity and is configured to sense the types of encountered tissue. Using the epidural access procedure as an example, device and method designs are presented, which enable the sensing of needle entrance to the epidural space and anchoring of the cannula within the ligamentum flavum tissue to prevent puncturing of the dura mater. In case of tissue sensing by an expandable balloon, balloon fluid pressure and volume are used to indicate tissue and cavity characteristics encountered during the procedure. Device embodiments, device construction methods and treatment methods are provided.

10 Claims, 37 Drawing Sheets

(51) Int. Cl.
*A61M 25/06* (2006.01)
*A61B 17/00* (2006.01)
*A61M 25/10* (2013.01)
*A61M 25/00* (2006.01)
*A61B 90/00* (2016.01)

(52) U.S. Cl.
CPC ...... *A61B 17/3476* (2013.01); *A61B 17/3494* (2013.01); *A61B 17/3496* (2013.01); *A61M 25/0105* (2013.01); *A61M 25/0606* (2013.01); *A61B 2017/00022* (2013.01); *A61B 2017/3456* (2013.01); *A61B 2017/3488* (2013.01); *A61B 2090/064* (2016.02); *A61M 25/1011* (2013.01); *A61M 25/10184* (2013.11); *A61M 2025/0003* (2013.01); *A61M 2025/0007* (2013.01); *A61M 2025/0018* (2013.01); *A61M 2025/0166* (2013.01)

(58) Field of Classification Search
CPC .......... A61M 25/0105; A61M 25/0606; A61M 25/1011; A61M 25/10184; A61B 17/3401; A61B 17/3403; A61B 17/3417; A61B 17/3476; A61B 17/3494; A61B 17/3496; A61B 2017/00022; A61B 2017/3456; A61B 2017/3488; A61B 2090/064
See application file for complete search history.

(56) References Cited

U.S. PATENT DOCUMENTS

2011/0125107 A1* 5/2011 Slocum .............. A61B 17/3401
604/272
2012/0209303 A1 8/2012 Frankhouser et al.

* cited by examiner

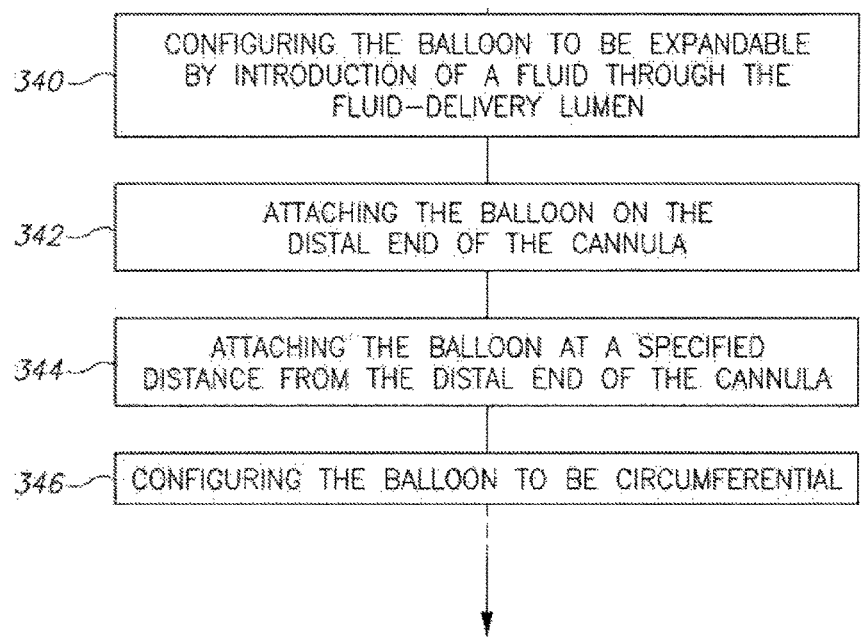
Figure 15 (cont. 1)

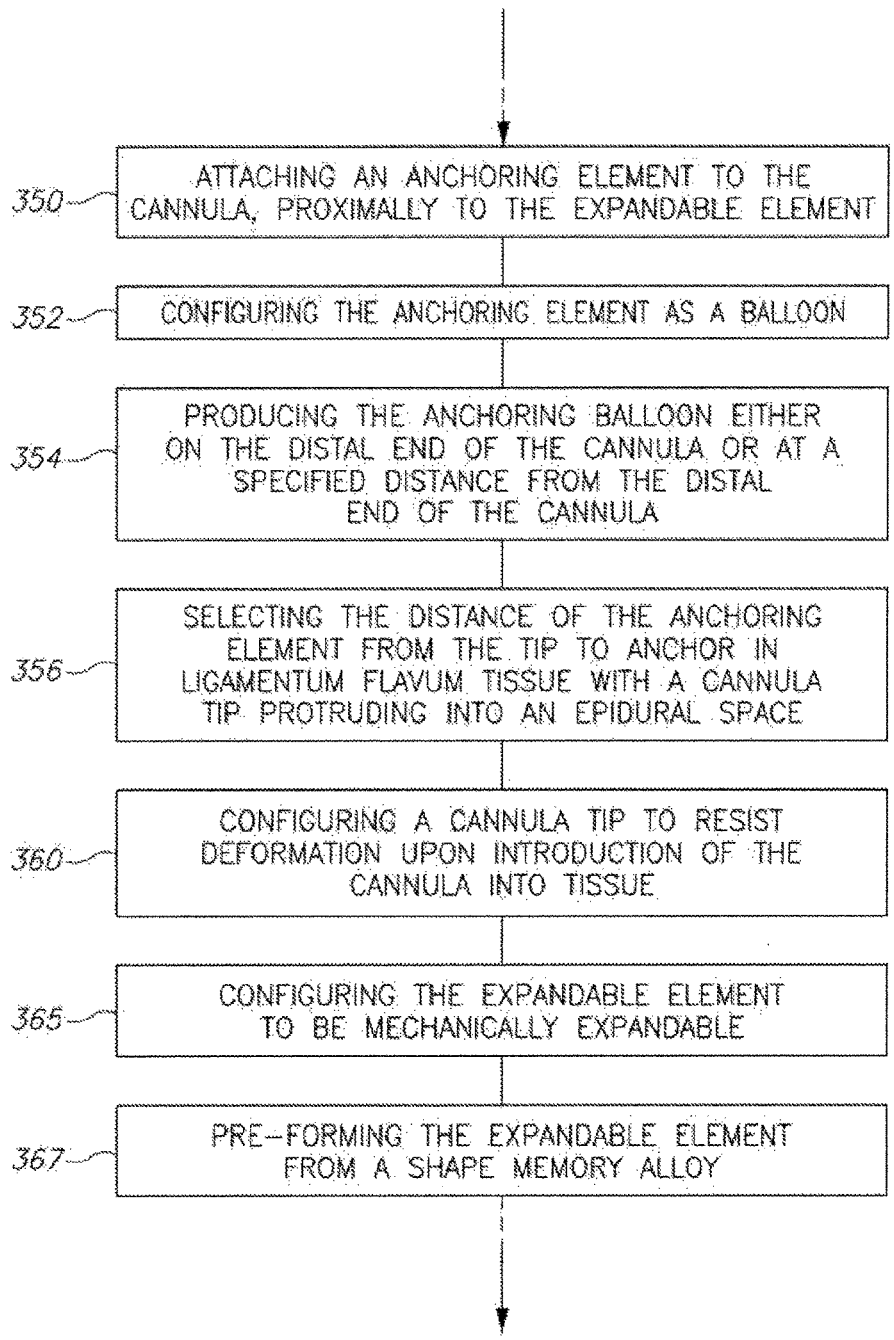
Figure 15 (cont. 2)

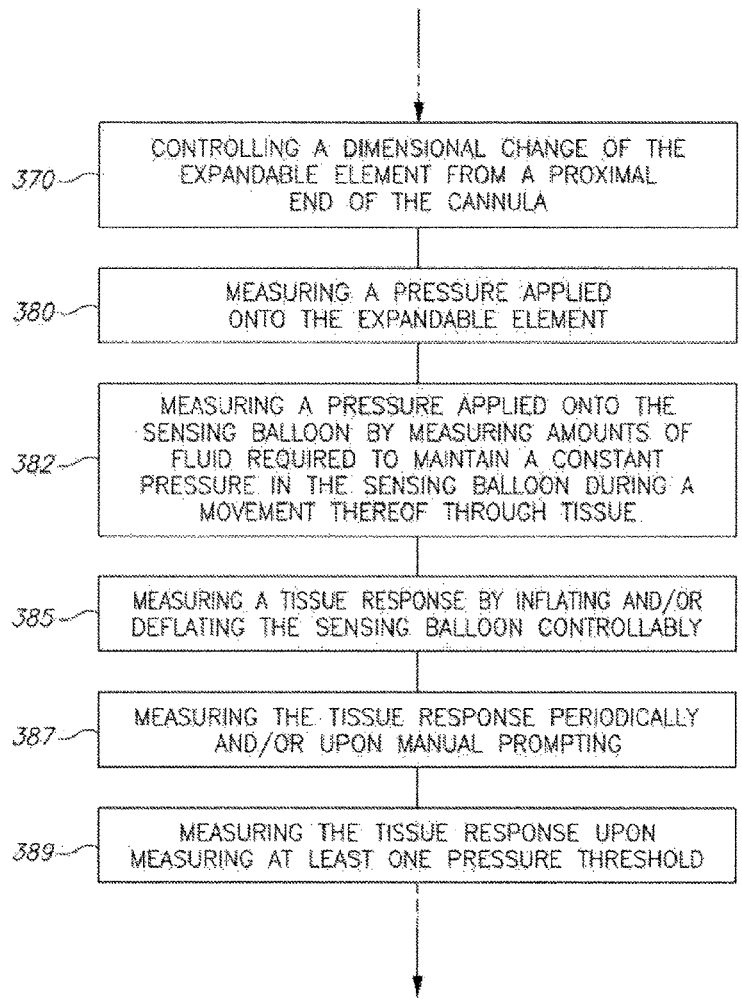
Figure 15 (cont. 3)

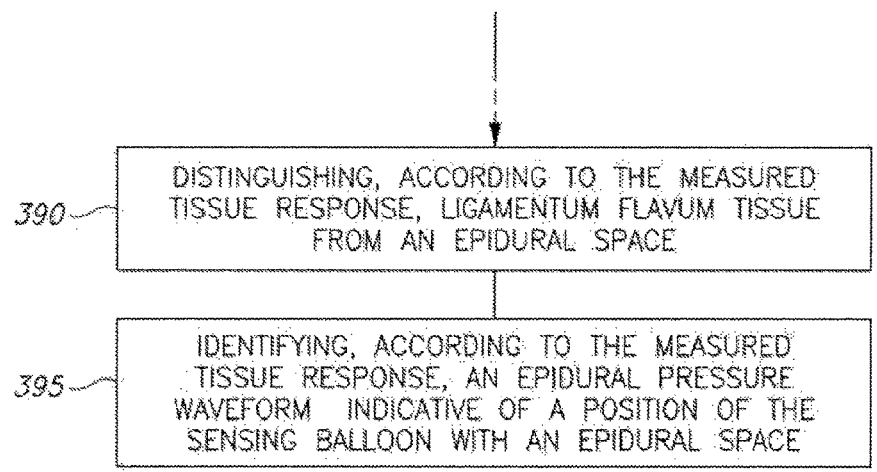
Figure 15 (cont. 4)

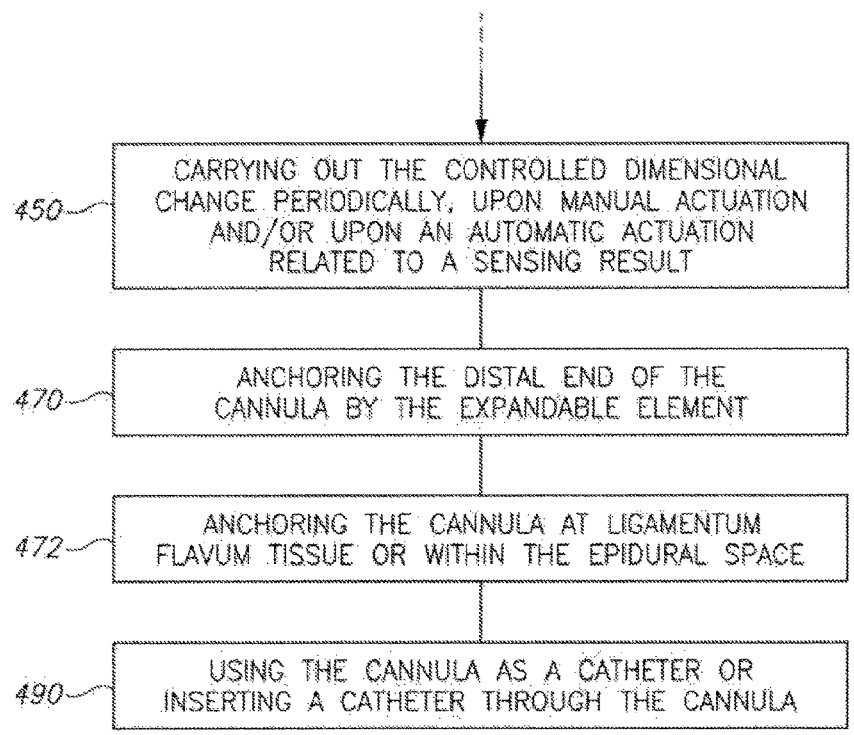
Figure 16 (cont. 2)

POSITIONING AND TISSUE SENSING DEVICES AND METHODS

CROSS-REFERENCE TO RELATED APPLICATIONS

This application is a National Phase Application of PCT International Application No. PCT/IL2013/051047, International Filing Date Dec. 22, 2013, claiming priority of U.S. Patent Application No. 61/745,561, filed Dec. 22, 2012, which is hereby incorporated by reference.

BACKGROUND OF THE INVENTION

1. Technical Field

The present invention relates to the field of medical devices, and more particularly, to a positioning device with sensing capacities.

2. Discussion of Related Art

FIG. 1A is a schematic illustration of the epidural space and surrounding anatomical structures with a needle properly inserted into the epidural space according to the prior art. FIG. 1A illustrates the final stage of an epidural access procedure. A tip 92 of a needle 94 is positioned inside epidural space 70, for administering a medication through syringe 90 into epidural space 70, after being inserted through skin 30 and advanced between spinous process 55 and through the subcutaneous fat layer 40, supraspinous ligament 50, interspinous ligament 52 and ligamentum flavum (LF) 60.

Overshooting of the tip of the needle beyond epidural space 70 may puncture dura mater 80 causing a leak of the cerebral-spinal fluid (CSF) from around spinal cord 85 into epidural space 70, leading to severe headaches (post dural puncture headaches syndrome).

The majority of current injection techniques are "blind" techniques, mainly tactile based. For example, the main technique of epidural access is based on the "loss of resistance technique" (LORT). In LORT, a fluid or air filled syringe is attached to a needle. While needle 94 is advanced through different layers in the insertion site, the physician taps on syringe 90. Inside dense ligament layers, the physician feels a strong resistance, but when crossing ligamentum flavum 60 and entering epidural space 70, there is a substantial loss of resistance so that the fluid or air from syringe 90 can be easily pushed into the low-pressured epidural space 70, thus signaling the physician to stop advancing needle 94.

FIGS. 1B-1E are schematically illustrated cross sectional views of the stages of a typical epidural access procedure, according to the prior art, including the penetration of ligamentum flavum 60 and including entering into epidural space 70. When needle 94 is advanced through ligamentum flavum 60, the elastic fibers of ligamentum flavum 60 are stretched by the pushing pressure exerted by needle 94 deep into epidural space 70, before entering epidural space 70 (see FIGS. 1C and 1D). When the fibers reach a certain displacement, ligamentum flavum 60 ruptures and needle 90 penetrates into epidural space 70, as depicted in FIG. 1E, typically stopping a short distance ($d_1$) from dura mater 80 (and in some cases even touching dura mater 80). The displacement required for the fibers of ligamentum flavum 60 to rupture differs from one person to another due to physiologic variations in ligamentum flavum elasticity, thickness and other factors. However, using the prior art technique has an extensive risk of accidently puncturing dura mater 80 due to overshooting of needle 94.

SUMMARY OF THE INVENTION

One aspect of the present invention provides a device comprising a cannula and a needle movable therethrough in a needle lumen of the cannula, wherein the cannula comprises an expandable element attached laterally at a distal end of the cannula, and a dimensional change of the expandable element is controllable from a proximal end of the cannula.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Figure 1A:
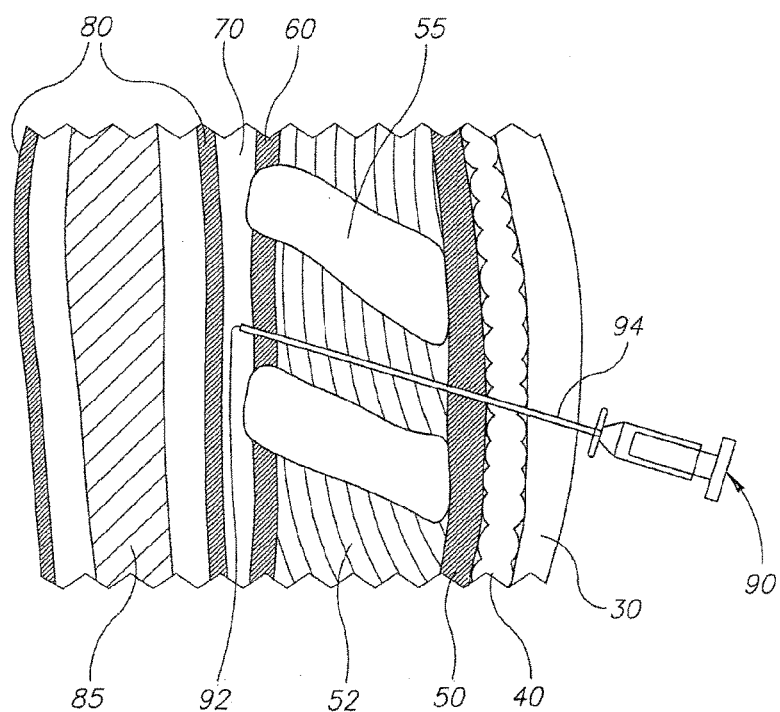
FIG. 1A is a schematic illustration of the epidural space and surrounding anatomical structures with a needle properly inserted into the epidural space according to the prior art.

Prior to the detailed description being set forth, it may be helpful to set forth definitions of certain terms that will be used hereinafter.

The term "fluid" as used in this application refers to gas or liquid, for example, air, water, inert gas, saline etc.

The term "expandable element" as used in this application refers to any element capable of being attached to a cannula and capable of changing at least one of its dimensions in a controllable manner.

The term "balloon" as used in this application refers to an expandable element having at least a partial outer shell and an inner volume configured to receive fluid and thereby change the pressure and/or volume of the expandable element. Both an expandable element in the general sense and the balloon as an embodiment of the expandable element are denoted in a non-limiting manner by the numeral 140. The use of the term "balloon" instead of the term "expandable element" is non-limiting and serves explanatory purposes only. The terms "sensing balloon" and "anchoring balloon" as used in this application refer to balloons serving a sensing function and an anchoring function, respectively. A sensing balloon and an anchoring balloon may be constructed and operated similarly or differently. In cases having both balloon types they are numbered 140A and 140B respectively, without limiting thereby any aspect relating to their construction or operation. Referring to "a balloon" or "an expandable device" may refer to either or both sensing balloon and anchoring balloon.

The term "dimensional change" as used in this application refers to any change in size or form of an expandable element, including both an increase in any of the dimensions of the expandable element (i.e. an expansion of the expandable element) as well as a decrease in any of the dimensions of the expandable element (i.e. a contraction of the expandable element). For example, in cases the expandable element comprises a balloon, the term "dimensional change" as used in this application refers to either inflation and/or deflation of the balloon.

The terms "expanding system" and "expanding mechanism" as used in this application refer to a system or mechanism arranged to change at least one dimension of the expandable element. The expanding system or mechanism may increase and/or decrease dimensions of the expandable element controllably.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

A positioning device with sensing capacities is provided, which facilitates needle or catheter introduction into a body tissue or cavity and is configured to sense the types of encountered tissue. Using the epidural access procedure as an example, device and method designs are presented, which enable the sensing of needle entrance to the epidural space and anchoring of the cannula within the ligamentum flavum tissue to prevent puncturing of the dura mater. In case of tissue sensing by an expandable balloon, balloon fluid pressure and volume are used to indicate tissue and cavity characteristics encountered during the procedure. Device embodiments, device construction methods and treatment methods are provided.

In certain embodiments, a device 100 is provided for performing a procedure of epidural access, including determining the type of one or all tissues the needle is advancing through, including interspinous ligament 52, ligamentum flavum 60 and inside epidural space 70, as well as indicating transition between tissues and cavities. Device 100 may be further adapted to allow determination of the type of one or more tissues that an elongated instrument is advancing through, as well as indicating transition between different tissues and cavities. Such devices can be found useful in various medical procedures, including, without limiting the scope of the invention, insertion of chest tubes, dental injection and drillings, central venous catheterization (CVC), arterial cannulation, laparoscopy, peritoneal penetration, biopsy of cancerous tissue, amniocentesis and lumbar puncture. In the field of epidural procedures, device 100 is designed to overcome major disadvantages of the "loss of resistance technique" (LORT) described above. In particular, using LORT, and because of the elastic properties ligamentum flavum 60, the elastic fibers are pushed by needle 94 and are stretched into epidural space 70. For this reason, the rupture of these fibers takes place deep inside the epidural space 70 increases the risk of an overshooting of needle tip 92 into dura mater 80. Moreover, the resolution of the non-controlled advancement-increments of needle tip 92 is very limited and differs extensively from one physician to another. Another disadvantage of LORT is the relatively high risk of a false loss of resistance, taking place for instance inside the ligamentum flavum 60 due to a small gaps or pockets of fat between adjacent fibers. The following devices, systems and methods overcome these disadvantages.

Figure 2:
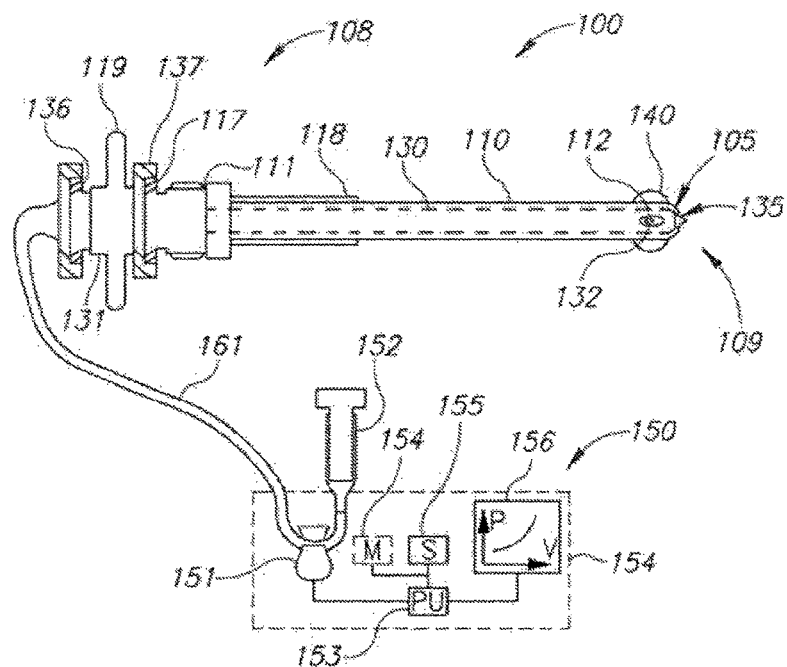
FIG. 2 illustrates a device comprising a disposable single lumen balloon cannula mounted over a needle and connected to an expanding system arranged to control a dimensional change of the expandable element, according to some embodiments of the invention.
Figure 3A:
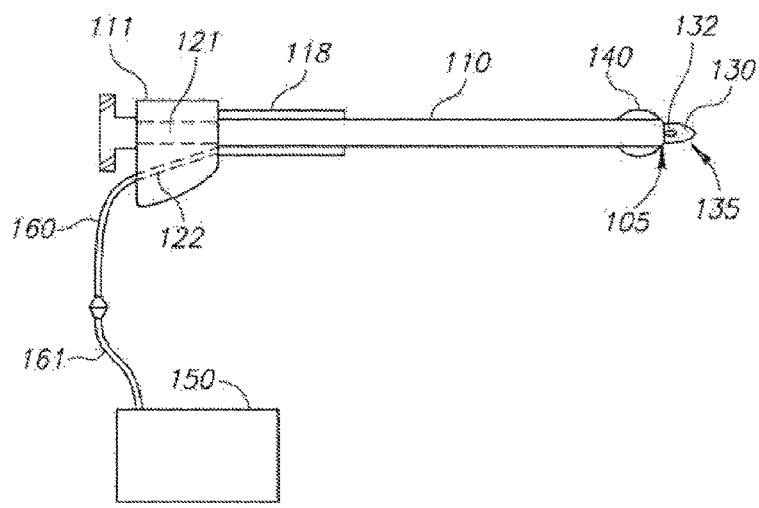
FIG. 3A is a high level schematic illustration of a disposable double lumen balloon cannula, according to some embodiments of the invention.
Figures 3B, 3C:
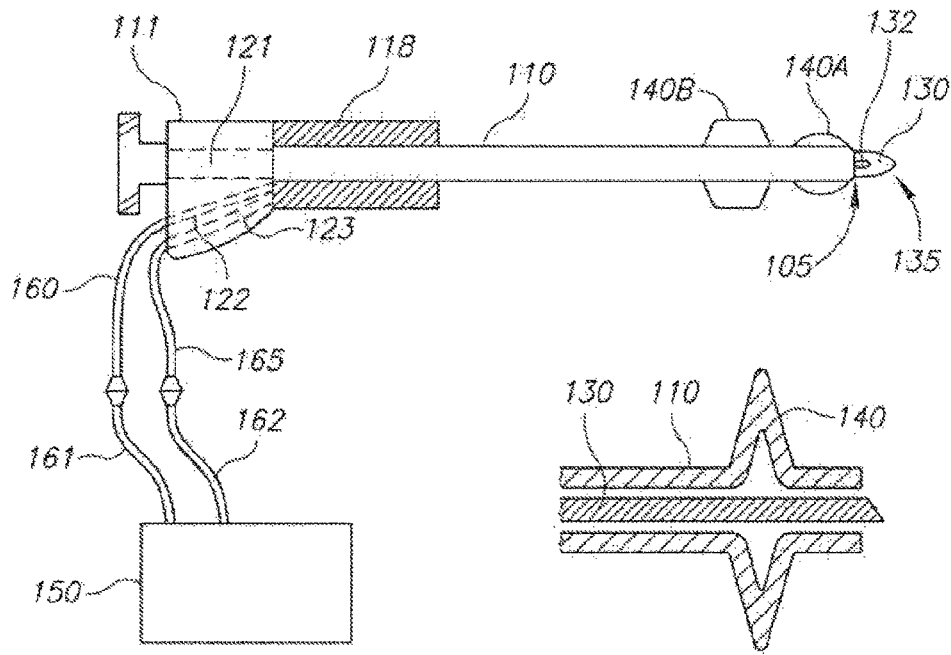
FIG. 3B illustrates a disposable double balloon cannula having three lumens, according to some embodiments of the invention.
FIG. 3C illustrates a mechanically expandable element according to some embodiments of the invention.
Figure 4:
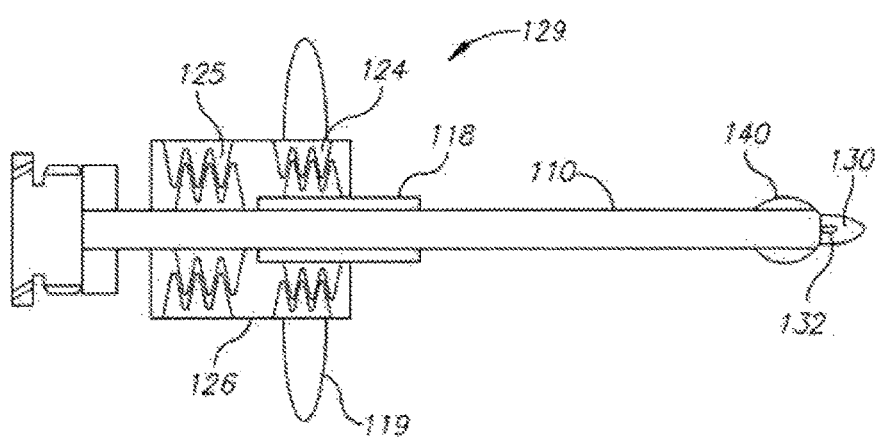
FIG. 4 is a high level schematic illustration of a device having an incremental advancing mechanism, according to some embodiments of the invention.

FIGS. 2, 3A-3C and 4 are high level schematic illustrations of devices 100, according to some embodiments of the invention. FIG. 3A is a high level schematic illustration of disposable double lumen balloon cannula 110, FIG. 3B illustrates a disposable double balloon cannula 110 having three lumens, FIG. 3C illustrates a mechanically expandable element 140, FIG. 4 illustrates device 100 having an incremental advancing mechanism 129 (see details below) and FIGS. 5A-5I are high level schematic illustrations of device longitudinal cross sections, according to some embodiments of the invention.

Certain embodiments comprise a device 100 comprising a cannula 110 and a needle 130 movable through cannula 110 in a needle lumen 121. Cannula 110 comprises an expandable element 140 attached laterally at a distal end 109 of cannula 110. A dimensional change of expandable element 140 is controllable from a proximal end 108 of cannula 110. In certain embodiments, expandable element 140 may be circumferential with respect to cannula tip 105.

Figure 5A:
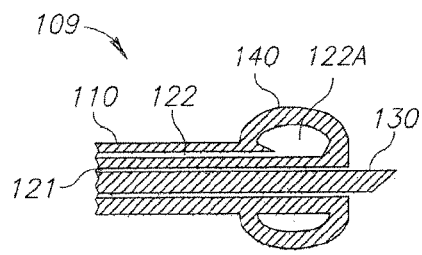
FIGS. 5A-5F are high level schematic illustrations of device longitudinal cross sections, according to some embodiments of the invention.
Figure 5B:
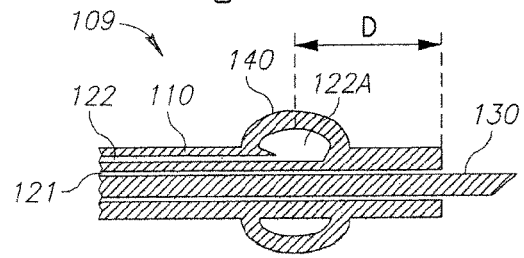
Figure 5C:
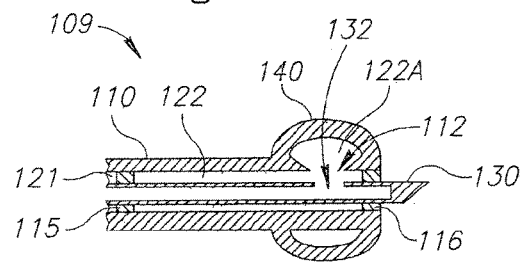

In certain embodiments, expandable element 140 may be a sensing balloon 140 or 140A, which is internally in fluid communication with a fluid-delivery lumen 122 and is expandable by introduction of a fluid through fluid-delivery lumen 122. Fluid-delivery lumen 122 may be integrated in different ways within the cannula-needle system, some of these ways are illustrated in the following non-limiting examples. For example, FIG. 5A schematically illustrates an internal lumen 122A of balloon 140 in fluid communication with fluid-delivery lumen 122 (in cannula 110) which is separate from needle lumen 121 in cannula 110. In another example, FIG. 5C schematically illustrates hollow needle 130 with a closed tip having an inner lumen 124 which is in fluid communication with fluid-delivery lumen 122 and may be used to deliver fluid into internal lumen 122A of balloon 140. In certain embodiments, fluid-delivery lumen 122 may be at least a part of needle lumen 121 of cannula 110. Such part, marked in FIG. 5C as fluid-delivery lumen 122, may be separated from the remainder of needle lumen 121 (marked in FIG. 5C as needle lumen 121), for example by sealing elements 115, 116. In certain embodiments, sealing elements 115, 116 exhibit a safety leakage threshold that limits the maximal fluid pressure that is allowed to build up in fluid-delivery lumen 122 and balloon 140.

Devices 100 are described in greater detail in the following.

FIG. 2 illustrates device 100 comprising disposable single lumen balloon cannula 110 mounted over needle 130 and connected to an expanding system 150 arranged to control the dimensional change of expandable element 140, according to some embodiments of the invention.

Expanding system 150 comprises of a pump 151, a sensor 155 and a micro-processor 153. It may also comprise a fluid container 152, an extra memory unit 154 and an indication device 156. Pump 151 may be arranged to controllably pump fluid such as gas (e.g., air) or liquid (e.g., saline or water) into and out of balloon 140. Pump 151 is preferably a peristaltic pump that pumps fluid into and out of balloon 140, e.g., by squeezing pump tubing 161 in a sterile manner, without having the fluid being in contact with pump 151. Container 152 may be used to hold fluid and is connected to pump tubing 161.

In certain embodiments, expanding system 150 may be arranged to measure a pressure applied onto expandable element 140, e.g. sensing balloon 140A, during a movement thereof through tissue.

Sensor 155 is arranged to measure physical parameters associated with balloon 140. In certain embodiments, sensor 155 may be placed inside housing 157 that contains pump 151 and micro-processor 153. In certain embodiments, sensor 155 may be mounted on a proximal end 108 of cannula 110 or needle 130, or in the vicinity of them. Such sensors 155 may be pressure sensors, force sensors, displacement sensors, strain gauges, tactile sensors, volume sensors, flow sensors, piezoelectric sensors or any other sensors arranged to provide data over fluid characteristics. In certain embodiments, two sensors 155 may be used, e.g., a pressure sensor and a flow sensor. The data collected by sensor 155 is sensed while balloon 140 exerts pressure onto portions of the mammalian tissue. The sensed data is of physical parameters associated with expandable device 140, and reflects mechanical properties of the tissue in which balloon 140 is disposed while obtaining the sensed data.

The measured physical parameters, associated with balloon 140, may comprise the instantaneous pressure inside balloon 140, the instantaneous volume of balloon 140, the frequency of the pressure applied on balloon 140, the displacement of balloon 140, the external force applied on balloon 140 by the mammalian tissue, spatial force or spatial pressure applied on balloon 140 or any other measurement indicative of the balloon or tissue characteristics.

Micro-processor 153 receives data from sensor 155 and controls pump 151. Micro-processor 153 may record, store and analyze the data received from sensor 155 in real-time or near real-time. The stored data and analyzed data may later be used as part of the documentation of the procedure, and may be outputted to a computer, a server, or a printer. The output of micro-processor 153 may be indicated to the operator in real-time through an indication device 156.

Such indication device may comprise any of a display, an LCD screen, a gage, a light indicator, an audio indicator and a tactile indicator. Alternatively or additionally, expanding system 150 may be connected either wirelessly or by a cable connection to a computer, a laptop, a tablet, a smartphone and a printer.

In certain embodiments, expanding system 150 may be arranged to measure a tissue response by inflating and/or deflating sensing balloon 140A controllably. Measuring the tissue response by expanding system 150 may be carried out periodically, upon manual prompting and/or upon specific pressure measurements using sensing balloon 140A (e.g., pressure measurements exceeding or below at least one pressure threshold). See for example FIGS. 7A-7C, 8 and 9 below for exemplary measurement procedures.

In certain embodiments, expanding system 150 may be arranged to distinguish, according to the measured tissue response, ligamentum flavum tissue from epidural space 70 (see for example FIG. 10 and corresponding explanations below). In certain embodiments, expanding system 150 may be arranged to identify, according to the measured tissue response, an epidural pressure waveform indicative of a position of sensing balloon 140A with epidural space 70 (see for example FIG. 11 and corresponding explanations below).

FIGS. 6A-6F are high level schematic transverse cross sectional illustrations of disposable balloon cannulas 110 of device 100, according to some embodiments of the invention.

In certain embodiments, distal end 109 of pump tubing 161 is connected to a proximal Luer 136 that is attached to needle 130. Cannula 110 may be a single lumen (having needle lumen 121 only, FIGS. 5C, 6A). Cannula 110 has proximal sealing element 115 and distal sealing element 116 that facilitate a sealable pathway for needle 130. Needle 130 is connected to cannula 110, preferably using a Luer lock fitting connection between Luer 117 that is part of hub 111 of cannula 110 and distal Luer 137 that is part of hub 131 of needle 130. Other coupling structures may be used, such as a friction fitting or a clip and a slot. In certain embodiments, cannula 110 may be permanently attached to needle 130 (i.e. using glue).

Fluid-delivery lumen 122 and needle lumen 124 may be interconnected by a distal perforation 132 in needle 130. The interlocking connection between cannula 110 and needle 130 is arranged in a way that opening 112 of fluid-delivery lumen 122 in cannula 110 is aligned with needle distal opening 132 of needle 130 (see FIG. 5C for a longitudinal cross sectional illustration). Due to sealing elements 115 and 116, once the fluid flows through pump tubing 161 and into needle 130, it continues to flow through opening 132 of needle 130 and fills cannula 110 between its two sealing elements. Thereafter, the fluid flows through opening 112 of cannula 110 into balloon 140. Such embodiments enable using the bore (inner lumen 124) of hollow needle 130 in order to pump gas or fluid into and out of balloon 140. Sealing elements 115 and 116 may be made of any material known in the art for preventing leakage, such as rubber. Alternatively, sealing elements 115, 116 may be attached to needle 130, in a manner that when needle 130 is inserted into cannula 110, sealing elements 115, 116 create a sealed space (122 in FIG. 5C) between needle 130 and cannula 110. Sealing elements 115 and 116 are configured to allow easy insertion and withdrawal of needle 130 through cannula 110. This may be achieved using materials with reduced friction, or by adjusting the dimensions of sealing elements 115 and 116 to carefully fit needle 130.

In certain embodiments, using a single lumen cannula having sealing elements may be advantageous since it enables reducing the outer diameter of cannula 110. In certain embodiments, cannula 110 has a diameter of between 1-3 mm, or of between 1-1.6 mm, and a length of between 60-160 mm, or of between 70-100 mm. When mounting cannula 110 on needle 130, tip 135 of needle 130 may be distal to tip 105 of cannula 110 by a distance of between 0.5-3 mm, or of between 0.5-1.5 mm. Cannula 110 may be designed in a manner that when mounted on needle 130 it has a sufficient compressive strength to withstand axially directed pushing forces facilitated by the opposing tissue. In some embodiments, wherein cannula 110 is used for performing the injection of medication or substances into a mammalian tissue after needle 130 is withdrawn, cannula 110 should be sufficiently soft and flexible so it does not disturb the patient during body movements. Additionally, cannula 110 should have a sufficient tensile strength in order to ensure a safe withdrawal of cannula 110 from the patient body. Lastly, cannula 110 should be kink-resistant to prevent inadvertent sealing due to kinking.

In certain embodiments, a cannula tip 105 may be arranged to resist deformation upon introduction of cannula 110 into tissue (see FIGS. 20A-20F below).

Cannula 110 may be made of any biocompatible material such as plastic, polyethylene, polyurethane, pebax or thermoplastic elastomers. Additionally, the structure of cannula 110 may be reinforced using a wire, a spring or a braided mesh made of stainless steel or nitinol alloy. The surface of cannula 110 may be coated using a hydrophilic coating, Polyurethane coating or PTFE coating in order to reduce the friction between cannula 110 and the surrounding tissue. Distal tip 105 of cannula 110 may be tapered in order to ensure easy insertion into tissue. In certain embodiments, cannula 110 may be coated with an antimicrobial coating to reduce the risk of infection, especially when using cannula 110 for a continuous infusion lasting for a few days. Cannula 110 may also have a flexible sleeve 118 located at the proximal end of cannula 110 to enable bending of proximal end when most of cannula 110 is positioned inside the body, while eliminating the risk of kinking. Such a feature will be desirable especially when using cannula 110 for a continuous infusion. In such case, the proximal end of cannula 110 may be attached to the body of the patient, for instance using a tape, creating an approximate 90 degrees angle.

In certain embodiments, balloon 140 may be a sensing balloon and/or an anchoring balloon, either being produced on distal end 109 of cannula 110. In certain embodiments, balloon 140 may be positioned at a specified distance D (FIG. 5B) from the distal end 109 of cannula 110. In certain embodiments, anchoring balloon 140B may be positioned at specified distance D from distal end 109 of the cannula 110, wherein specified distance D is selected to anchor anchoring balloon 140B in ligamentum flavum tissue with cannula tip 105 protruding into epidural space 70 (e.g., for dispensing medical fluids or for supporting catheter introduction into epidural space 70).

Either balloon may be circumferential with respect to cannula 110 or be expandable over a specified angular range (e.g. 270°, 180°, 90° etc.).

Figure 5D:
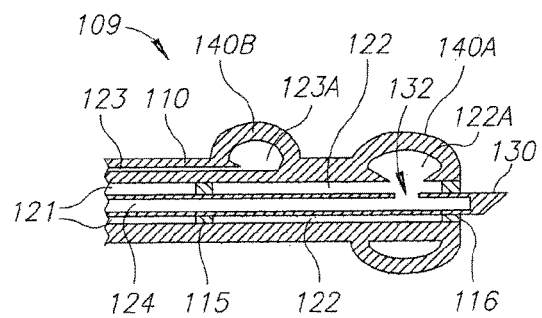
Figure 5E:
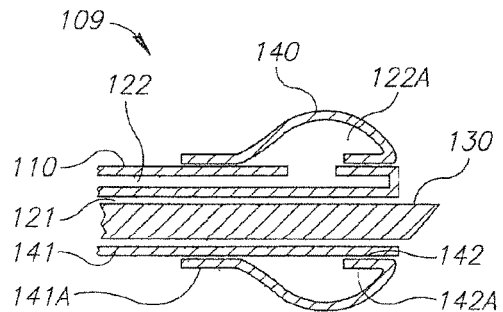
Figure 5F:
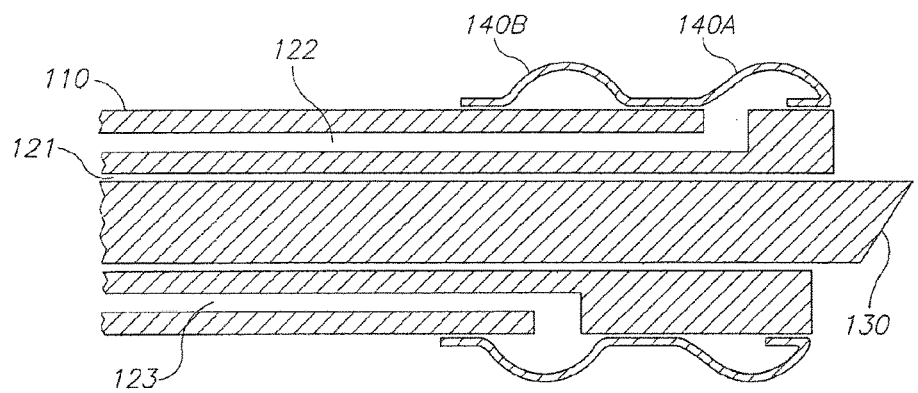
Figure 5G:
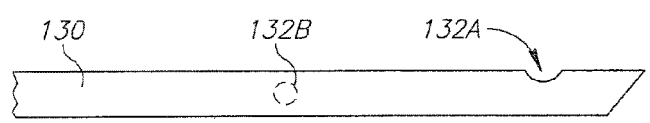
FIG. 5G is a high level schematic illustration of a controllable element that directs fluid to one or another of balloon connections, according to some embodiments of the invention.
Figure 5H:
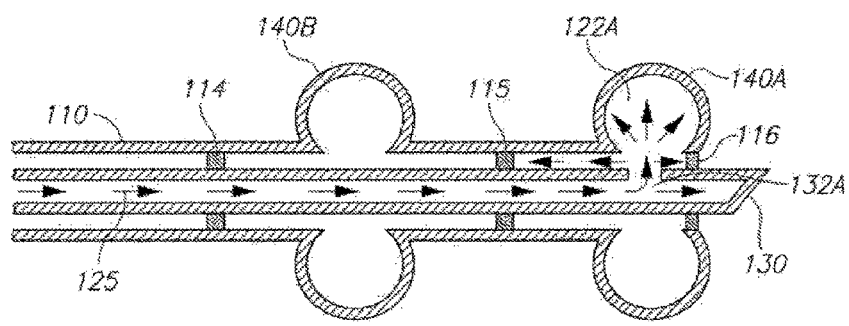
FIG. 5H-5I are a high level schematic illustrations of device longitudinal cross sections, having a controllable element that directs fluid to one or another of balloon connections, according to some embodiments of the invention.
Figure 5I:
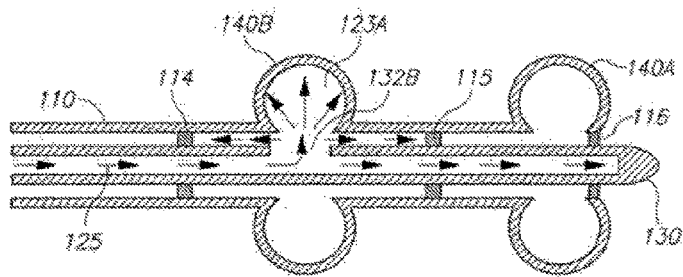

In certain embodiments (FIGS. 5H-5I), single lumen cannula 110 may be designed to enable inflating and deflating both balloon 140A, 140B, e.g. by means of a controllable element that directs fluid 125 to one or another of balloon connections to cannula 110, or by selecting balloon positions and flexibilities in a way that directs fluid 125 first to one of the balloons and then to the other, or proportionate the inflation of the balloon in a certain pre-configured manner. Controllable element 130 may be a needle having a closed tip and a single lumen 124 with at least two openings 132A and 132B. Openings 132A and 132B have an angle between them, e.g., 90 degree, relative to the longitudinal axis of controllable element 130 (FIG. 5G). Proximal sealing element 115, distal sealing element 116 and middle sealing element 117 define a sealable pathway for fluid 125 when either opening 132A or 132B of controllable element 130 is aligned with opening 112A or 112B of cannula 110 respectively. Sealing elements 115-117 may be either an integral part of cannula 110 or of controllable element 130. A $1^{st}$ position of controllable element 130 inside needle lumen 121 (FIG. 5H) controls the inflation of balloon 140A, whereas a 90 degrees rotation of controllable element 130 clockwise switches over the control to balloon 140B (FIG. 5I). Alternatively, rotation of cannula 110 relatively to controllable element 130 switches over the control between the two balloons.

Balloon 140 may be expanded to a preconfigured volume and shape. In certain embodiments, balloon 140 may have a length of between 2-5 mm, and a diameter of between 2-6 mm when fully expanded. The working pressure of balloon 140 may be between 0-2 bar, or between 0-0.3 bar. Balloon 140 may be securely attached to the external circumference of cannula 110, proximal to distal tip 105 of cannula 110, for example between 0.1-2 mm posterior to distal end 109 of cannula 110, whereas opening 112 of cannula 110 communicates with interiors 122A of balloon 140. Balloon 140 may be made of any biocompatible material such as polyurethane, silicone rubber, flexible PVC, PET, nylon, nylon elastomers and thermoplastic elastomers.

In certain embodiments, needle 130 may be an epidural needle, a spinal needle, a Tuohy needle, a Whitacre needle, a Sprotte needle, a biopsy needle, a Veress needle, or any other needle known in the art. Optionally, cannula 110 facilitates a pathway for other elongated members comprising e.g., a trocar, a surgical instrument, a catheter, a guidewire, an endoscope, an optical fiber or a miniature camera, to thereby facilitate visualization of a tissue or a cavity, a vascular cannulation or any other sharp object facilitated to be inserted into at least one mammalian tissue.

In certain embodiments, needle 130 may be a small gauge needle having a 22-27 gauge and have a pencil point tip 135. The combination of a small gauge needle together with a pencil point tip has been proven to reduce the risk of post dural puncture headache in case of an inadvertent puncture of dura mater 80. Additionally, a small gauge needle assists in reducing the tenting phenomenon of an elastic tissue prior to penetrating it. The length of needle 130 may be between 60-160 mm.

Figure 22A:
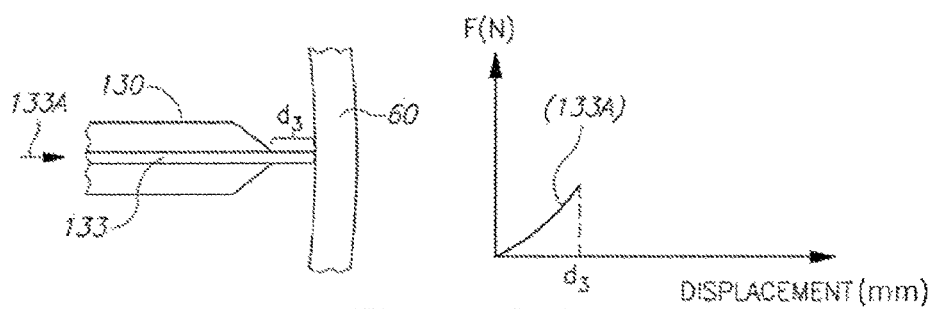
FIGS. 22A-22C are high level schematic illustrations of using a stylet to safely enter the epidural space, according to some embodiments of the invention.
Figure 22B:
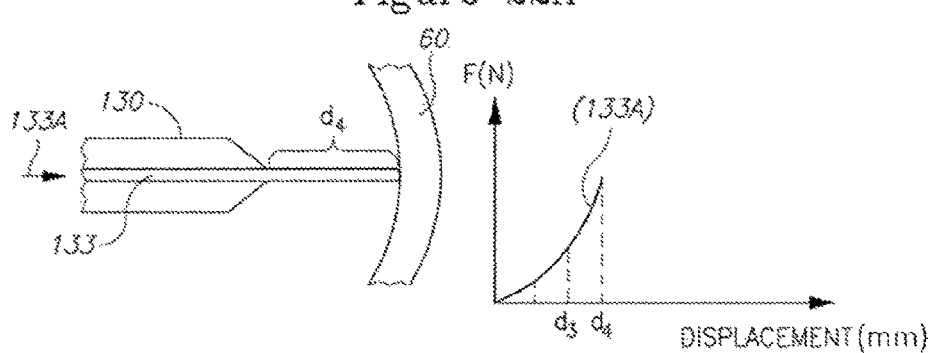
Figure 22C:
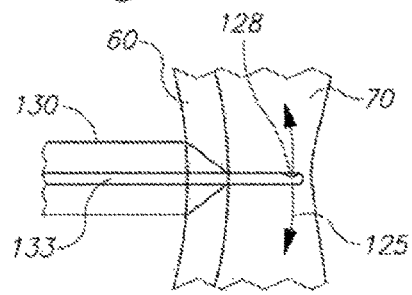
Figure 22D:
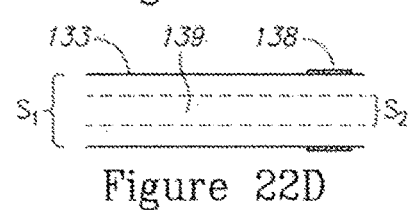
FIGS. 22D-22G are high level schematic illustrations of stylet configurations according to some embodiments of the invention.

Needle 130 may be a hollow needle having a bore lumen 124. A stylet 133 (see below, FIGS. 22A-22C) may be inserted inside hollow needle 130 in order to stiffen device 100, so to resist deflection and provide extra support during advancement through different tissues. In certain embodiments, wherein bore lumen 124 of needle 130 is used for inflation of balloon 140 (FIG. 5C), upon reaching a dense ligament, stylet 133 should be withdrawn in order to facilitate a pathway for fluid into balloon 140. After detecting epidural space 70 using device 100 and positioning of tip 105 of cannula 110 inside epidural space 70, needle 130 is withdrawn and fluid inside balloon 140 may be released into epidural space 70. Then, a syringe or a catheter extension may be connected to cannula 110, for example using Luer lock connection 117, and a medication is administered into epidural space 70. Alternatively, an epidural catheter may be threaded through lumen 121 of cannula 110 in order to administer medication.

In certain embodiments (FIGS. 18A-18D), balloon 140 may be attached directly to needle 130 without the use of a cannula and is inflated through lumen 124. At least one needle opening 132A or 132B is in fluid communication with interiors 122A of balloon 140. A stylet 133 is disposed inside lumen 124 of needle 130. The stylet is comprised of an elongated body 133A having a smaller diameter than lumen 124, thus enabling fluid pathway through needle opening 132A into interiors 122A. Distal end 133B of stylet 133 has a bigger diameter than elongated body 133A. Distal end 133B seals tip 135 of needle 130 and thus prevents fluid leakage through tip 135 and enables to maintain desired volume and pressure inside interiors 122A of balloon 140. Stylet 133 is connected to hub 170, wherein hub 170 is comprised of a connector 171 and inflation tube 172. Connector 171 can be, for example, a luer lock connection, and is connected to needle hub 131. Inflation tube 172 is attached to hub 170 and delivers fluid through hub 170 into lumen 124 of needle 130 while stylet 133 is connected to needle 130. After detecting epidural space 70 using device 100 and positioning of tip 135 of needle 130 inside epidural space 70, connector 171 of hub 170 is released from connector 136 of needle 130, and stylet 133 is withdrawn so that fluid inside balloon 140 may be released into epidural space 70. Then, a syringe may be connected to needle 130, for example using Luer lock connection 136, and a medication is administered into epidural space 70. Alternatively, an epidural catheter may be threaded through lumen 124 of needle 130 in order to administer medication.

Figure 3D:
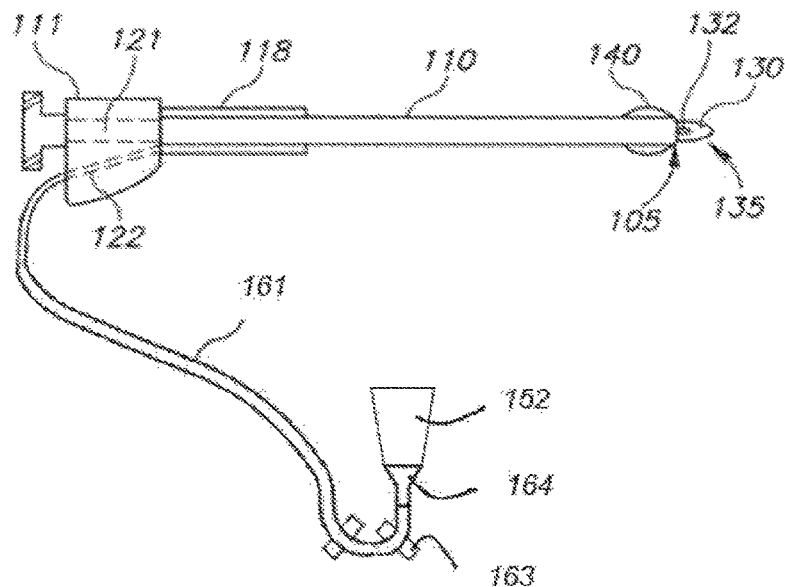
FIG. 3D is a high level schematic illustration of a disposable double lumen balloon cannula with a single tube connection, according to some embodiments of the invention.

FIG. 3A schematically illustrates a disposable double lumen balloon cannula 110, wherein a first lumen 121 facilitates a pathway for the insertion of various elongated instruments such as needle 130, and wherein a second lumen 122 facilitates a pathway for insertion and evacuation of fluid into sensing balloon 140. The configuration illustrated in FIG. 3A may be used to supply fluid into cannula designs as illustrated in FIGS. 5A, 5B, 5D and 5E. Cannula 110 may have a coaxial configuration, illustrated in cross sectional view in FIGS. 6B and 6E (the latter has supports 198 that reduce tendency of exterior wall 128 to collapse due to radial pressure), or an eccentric configuration illustrated in FIG. 6C. Second lumen 122 may be reached through side port 160 of cannula 110. Pump tubing 161 connects to side port 160 to supply fluid or gas from expanding system 150 to balloon 140. The connection may be achieved using a Luer lock fitting connection or using any other fitting. In another embodiment (FIG. 3D) the side port 160 and Pump tubing 161 can be replaced by a single tube 161 that can be attached to a peristaltic pump that pumps fluid into and out of balloon 140, by squeezing tube 161 in a sterile manner, without having the fluid being in contact with pump 151. The single tube may comprise two bullets 163 at the pump side to safely secure single tube 161 to pump 151. A container 152 for holding fluid is connected to single tube 161 through a connector 164. Container 152 may be a flexible bag with fluid inside, such as an infusion bag, that enables to pump in or pump out fluid from cannula lumen 122 while reducing air bubbles entering the lumen. In addition connector 164 enables manual emptying of lumen 122 and balloon 140 by connecting a syringe.

In certain embodiments, needle 130 may be solid with no bore. A solid needle may be advantageous since it cannot carry debris of tissue from one location to another, thus reducing the risk of contamination. This can be beneficiary when penetrating the spinal canal which is an extremely sensitive anatomical location. In addition, a solid needle may supply an increased support in order to resist deflection during advancement through the different ligaments.

Upon detection of epidural space 70 using device 100 and positioning of tip 105 of cannula 110 inside epidural space, medication may be administered directly via needle 130, wherein needle 130 is a hollow needle. Alternatively, or in an embodiment wherein needle 130 is a solid needle, needle 130 is withdrawn, while balloon 140 maintains its expanded state, thus preventing cannula 110 from migrating backwards into ligamentum flavum 60. A syringe or a catheter extension is then connected to cannula 110, for example using Luer connection 117, and a medication is administered to epidural space 70. Alternatively, an epidural catheter may be threaded through cannula 110 to administer such medication.

In certain embodiments, device 100 may further comprise an anchoring element such as an anchoring balloon 140B attached to cannula 110 proximally with respect to expandable element 140 such as sensing balloon 140A. A non-limiting example is illustrated in FIGS. 3B and 5D. Anchoring element may comprise anchoring balloon 140B which is internally 123A in fluid communication with a fluid-delivery lumen 123 and is expandable by introduction of a fluid therethrough. Fluid-delivery lumen 123 of anchoring balloon 140B may be cannula lumen 123 which is separate from needle lumen 121 of cannula 110 (FIG. 5D). Anchoring balloon 140B with fluid-delivery lumen 123 may be implemented independently of sensing balloon 140A with fluid-delivery lumen 122, or in relation thereto. For example, fluid-delivery lumens 122 and 123 may be in fluid communication or at least partly overlap, or balloons 140A, 140B may be parts of a single balloon or be the same balloon under different pressurization conditions.

Figure 6A:
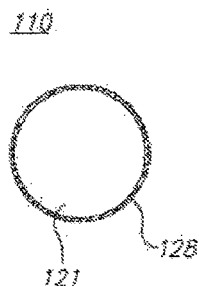
FIGS. 6A-6F are high level schematic transverse cross sectional illustrations of disposable balloon cannulas of the device, according to some embodiments of the invention.
Figure 6B:
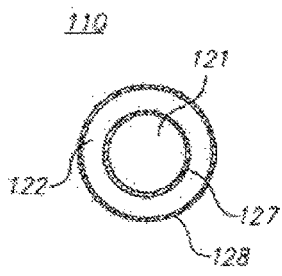
Figure 6C:
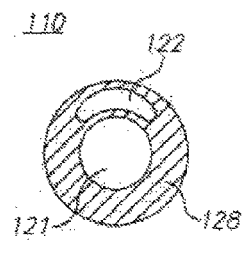
Figure 6D:
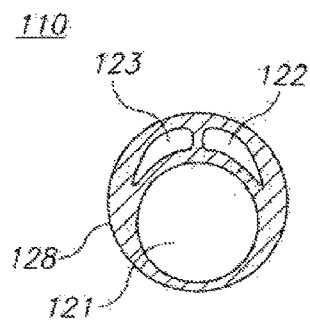
Figure 6E:
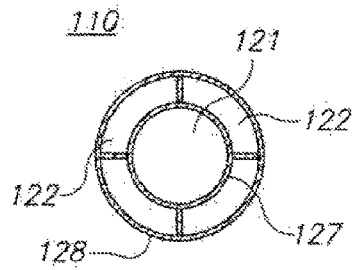
Figure 6F:
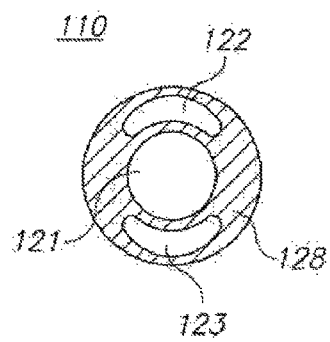

FIG. 3B schematically illustrates a disposable double balloon cannula 110 having three lumens, wherein one lumen 121 facilitates a pathway for the insertion of various elongated instruments such as needle 130, a second lumen 122 facilitates a pathway for the insertion and evacuation of fluid into sensing balloon 140A, and wherein a third lumen 123 facilitates a pathway for the insertion and evacuation of fluid into anchoring balloon 140B. An exemplary configuration of the cross section of cannula 110 is illustrated in FIGS. 6D and 6F. FIG. 5F illustrates a longitudinal cross section that relates to FIG. 6D Sensing balloon 140A and/or anchoring balloon 140B may be expanded to a preconfigured volume or shape. They may be made of any biocompatible material known in the art, such as polyurethane, silicone rubber, flexible PVC, PET, nylon, nylon elastomers and thermoplastic elastomers. In certain embodiments, expandable element 140 may comprise expandable sensing and/or anchoring element(s) 140A, 140B (not necessarily sensing and/or anchoring balloons 140A, 140B, respectively) made of a shape memory alloy, such as NiTi alloy, which expands under certain conditions. Expandable element 140 may be expanded using a mechanical mechanism that is based on springs or any other mechanical element. In certain embodiments (e.g., FIG. 3C), expandable element 140 may be mechanically expandable. In certain embodiments, expandable element 140 may be pre-formed from a shape memory alloy such as nitinol, which is in a naturally expanded state, unless a radial biasing force is applied on it. In certain embodiments, expandable element 140 will remain contracted when inside dense ligaments that exert radial force against it, and will expand upon introduction of expandable element 140 into epidural space 70.

Sensing balloon 140A may be securely attached to the external circumference of cannula 110, proximal to distal tip 105 of cannula 110. For example, distal tip of balloon 140A may be at distance D of between 0.1-3 mm posterior to distal tip 135 of needle 130 in a manner that tip 135 cannot puncture balloon 140A. Anchoring balloon 140B may be securely attached to the external circumference of cannula 110, while distal tip of balloon 140B is located at a distance D of between 1-20 mm from distal tip 135 of needle 130, e.g., between 4-8 mm. Anchoring balloon 140B may have a diameter of between 3-10 mm and a working pressure of between 0.01-2 bar, e.g., between 0.01-0.26 bar. Anchoring balloon 140B may have various shapes designed for securely anchoring it inside the tissue, including a dog-bone shape. Cannula hub 111 of cannula 110 may be sealed except for one opening of lumen 121. Cannula hub 111 may have a Luer lock fitting connection 117 designed for securing cannula 110 to needle 130, and for connecting either a syringe or a catheter extension for the administration of liquid or medicine after withdrawal of needle 130 or for drainage of body fluids. When cannula 110 is installed over needle 130, it may be fixed to needle 130 so that they both move as one unit through the body tissues.

Inflation of sensing balloon 140A and anchoring balloon 140B may be performed using expanding system 150 having inflation pump tubing 161 and 162 that are connected, e.g., via Luer lock fitting connections to side ports 160 and 165 of lumens 122 and 123 respectively. Alternatively, balloons 140A and 140B may be inflated using long inflation tubes (instead of short side ports) that connect to expanding system 150. Expanding system 150 may comprise two pumps (not shown) for controllably pump fluid or gas into and out of balloons 140A and 140B. Alternatively, anchoring balloon 140B may be inflated manually using a syringe.

Upon detection of epidural space 70 by device 100, micro controller 153 may activate pump 151 to immediately expand anchoring balloon 140B to reach a predetermined pressure of between 0.1-2 bar. Anchoring balloon 140B may be anchored inside ligamentum flavum 60, thus preventing inadvertent advancement of needle 130 into dura mater 80 and facilitating the fixation of cannula 110 inside epidural space 70.

Alternatively, expansion of anchoring balloon 140B may be performed according to a decision of the operator, either manually using a syringe, or semi-automatically using expanding system 150. In certain embodiments, needle 130 is then withdrawn out of cannula 110, and cannula 110 is connected to extension catheter for continuous infusion of medication into epidural space 70. Alternatively, an epidural catheter may be threaded through cannula 110 to administer such medication In certain embodiments, a disposable double balloon cannula 110 may be implemented using two lumens 121 and 122, so that one balloon, either sensing balloon 140A or anchoring balloon 140B is inflated through lumen 122, while the second balloon is inflated through an elongated member passing through lumen 121 as described in FIG. 5D.

In the present, big gauge needles (16-18 gauge) are required to perform epidural injections due to several reasons: a large needle bore is required in order to perform the loss of resistance technique (LORT), which is necessary for the identification of the needle's position; a large bore is required for threading an epidural catheter through the needle and into the epidural space; the needle needs to resist deflection that may occur due to the dense ligaments being penetrated. Advantageously, device 100 enables the use of small gauge needles since LORT is no longer necessary for detecting the needle location; cannula 110 enables a wide path for insertion of an epidural catheter; cannula 110 may function as the catheter itself, so to replace the need for threading a catheter; and the combined structure of cannula 110 together with needle 130 may provide enough stiffness to cope with deflection.

Prior to a procedure of placing a needle or a cannula inside epidural space 70, cannula 110 may be installed over needle 130 by inserting needle 130 through lumen 121 of cannula 110, coupling of needle 130 and cannula 110 (e.g., by an interlocking structure) and connecting cannula 110 to expanding system 150, using pump tubing 161. In certain embodiments, cannula 110 and needle 130 may be already installed together and packed in a sterile disposable kit, possibly together with disposable pump tubing 161, a disposable fluid container 152, and various Luers and connectors. In such an embodiment, the operator may be able to open the kit, manually pump saline into container 152 (e.g. a syringe), connect proximal end of pump tubing 161 to container 152, connect distal end of pump tubing 161 to cannula 110, mount container 152 in a specified location on expanding system 150, push a designated section of pump tubing 161 into a designated location in pump 161, and switch on expanding system 150 to facilitate performing the procedure using device 100. In another embodiment, pump tubing 161 is an integral part of cannula 110, having only a connector on its proximal end that connects to container 152. Container 152 may also be a saline filled bag, thus saving the step of manually pumping saline to container 152.

Advantageously, device 100 is an improvement over other devices that measure pressure through an open tip of a needle, since this pressure can easily be biased due to the small contact area between the tip and the surrounding tissue. Moreover, during the advancement of the needle, its tip is often occluded by small pieces of tissue that obscure the real pressure in the surrounding tissue. Lastly, when measuring pressure through an open tip, the fluid or gas used for performing the measurement is spread inside the surrounding tissue, therefore changing the environment and biasing the objectivity of the measurement, as well as increasing the risk of a contamination carried through the fluid.

Using a closed system such as balloon 140 for performing measurements associated with the surrounding tissue has several additional advantages. First, having a balloon such as sensing balloon 140 at the circumference of the needle helps gathering significantly more data due to the large contact area formed between the balloon and the surrounding tissue, thus enables integrated readings of the surrounding pressure and reduces bias. Second, balloon 140 is not sensitive to an occlusion of tip 135 of needle 130. Third, due to the use of a closed system, the environment is unchanged since no fluid is spread and the risk of contamination carried by the fluid is eliminated. Fourth, a measurement of the mechanical resistance of a tissue using balloon 140 may be done when balloon 140 exerts substantial pressure on surrounding tissue in order to displace said tissue, thus amplifying the resistance of elastic tissues and assisting in differentiating them from non-elastic tissues. Fifth, using balloon 140 enables to conduct different types of measurements in a single location, for example during different dimensional changes of the balloon, such as contraction and expansion of the balloon. Sixth, balloon 140 enables the use of small gauge needles. Seventh, friction forces that operate on the body of cannula 110 or needle 130 have no influence on the measurement performed by balloon 140.

Referring back to the procedure of epidural access, in certain embodiments, needle 130 may be advanced through the different tissues while sensing balloon 140, which is preferably filled with fluid such as saline, engages with the surrounding tissue. Pressure and volume inside the balloon 140 are measured using sensors 155, such as pressure sensor, flow meter, or any other sensors known in the art. According to the volume and pressure of sensing balloon 140, the type of tissue engaging with sensing balloon 140 may be determined. The pattern of change in pressure and volume of balloon 140 during advancement of cannula 110 and needle 130 may be used to indicate transitions between tissues as well as entrance of needle 130 into a low dense space, such as epidural space 70. In certain embodiments, a standard syringe containing air or saline may be attached to hub 131 of needle 130 and may be used by the physician to perform the loss of resistance technique (LORT) while advancing the needle. Upon crossing ligamentum flavum 60 with needle tip 135 and entrance into epidural space 70, a sudden drop in pressure occurs in sensing balloon 140. As a result, expanding system 150 immediately inflates sensing balloon 140, thus preventing inadvertent advancement of needle 130 into dura mater 80, due to the large surface area formed between balloon 140 and the tissues inside epidural space 70 (e.g. epidural fatty tissue). According to certain embodiments, anchoring balloon 140B is automatically and controllably expanded upon detection of epidural space 70, in order to engage with the surrounding tissue, e.g., ligamentum flavum 60, and to exert pressure onto it in a manner that locks cannula 110 and, consequently, needle 130 in place, and prevent inadvertent puncture of Dura mater 80. In addition, an alert such as an acoustic or visual indication is given to the physician.

A second verification of the location of needle 130 and cannula 110 may be performed by detection of the epidural pressure waveform (EPWF) that is unique to epidural space 70. If the EPWF is not detected, the physician should receive an indication that the device is not correctly placed. This second verification can prevent major complications such as inadvertent placing of needle 130 inside a blood vessel or inside the subarachnoid space, which can result in paralysis or even death. In other embodiments, the physician needs to inject a predefined amount of saline through needle 130 or through cannula 110, for example 5 ml, prior to verification of the EPWF using sensing balloon 140. The injected saline may act as a medium that enables better transmission of the EPWF to sensing balloon 140. If the detection of epidural space 70 is positive, the physician can detach the syringe and inject an anesthetic or medication through needle 130. Alternatively, needle 130 is withdrawn by the physician, leaving cannula 110 inside epidural space 70. The physician can connect a syringe or a catheter extension to cannula 110, and administrate anesthetic or medication directly to epidural space 70, either a single shot or for continuous infusion.

In certain embodiments, additional instruments may be threaded through lumen 121 once needle 130 is removed, such as catheters, leads for neuro-stimulation, optic-fibers etc. While currently threading a catheter through a needle could result in breakage or shearing of the catheter due to contact between the catheter and the bevel of the needle, a clear advantage of using cannula 110 as a path for insertion of instruments or smaller catheters to a desired location is that its blunt tip 105 doesn't jeopardize the inserted instrument or catheter. Furthermore, anchoring cannula 110 ensures and supports correct insertion of the instrument.

In an epidural access procedure, one of the many challenges is inserting a needle through a path that leads to epidural space 70. However, given the blind nature of the procedure, the physician can easily lose his orientation and inadvertently advance the needle through a wrong path that will surely miss epidural space 70. Advantageously, in the present invention, since the tissue engaged with balloon 140 is detected, the physician can be alerted when a tissue is encountered which is not part of the planned path. Such an early indication assists the physician in correcting the needle's path, to once again engage with tissues that are part of the path leading to epidural space 70, such as supraspinous ligament 50, intraspinous ligament 52 or ligamentum flavum 60.

The measuring of the physical parameters, associated with sensing balloon 140, may take place automatically during advancement of cannula 110 while sensing balloon 140 is either in an expanded state or a semi-expanded state (partially inflated). Additionally or alternatively, the measurement may take place when cannula 110 is static in one unknown location. In such case, the measurement may be taken when sensing balloon 140 is in a steady expanded state or semi-expanded state, or during the expansion or contraction of balloon 140 wherein balloon 140 exerts pressure onto surrounding tissue in a manner that create a displacement in the tissue, in order to extract mechanical parameters associated with the elasticity of surrounding tissue. The measurement may take place upon a decision of the operator, for example by pressing a button or a paddle, when sensing balloon 140 is static inside an unknown tissue, or it may be taken automatically by expanding system 150 and microprocessor 153, in response to different triggers such as a time driven measurement or an event driven measurement (e.g. change in measured parameters).

In certain embodiments, determining the type of tissues as well as transitions between different tissues and cavities are facilitated using the sensing and measurement methods described herein. As a non-limiting example, the following method describes the steps of an epidural access procedure according to some embodiments of the invention. During epidural access procedure, a physician performs procedural steps, in order to differentiate between ligamentum flavum 60 and epidural space 70, wherein a principal intention of the epidural access procedure is to be able to stop the advancement of needle 94 upon entering epidural space 70.

Figure 7A:
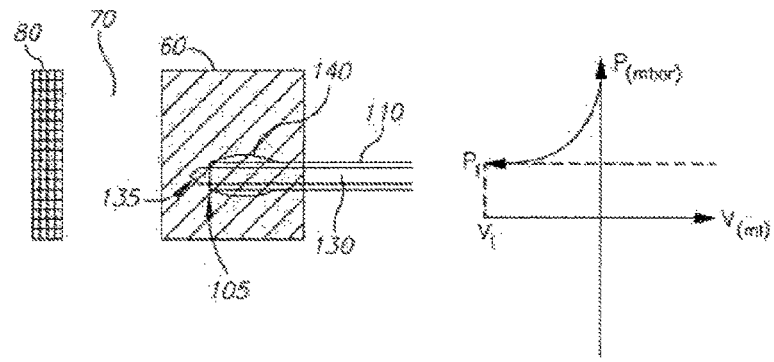
FIGS. 7A-7C are high level schematic illustrations of a behavior of a sensing balloon when disposed inside different tissues, as well as graphs that describe the pressure vs. volume curves of the sensing balloon, according to some embodiments of the invention.
Figure 7B:
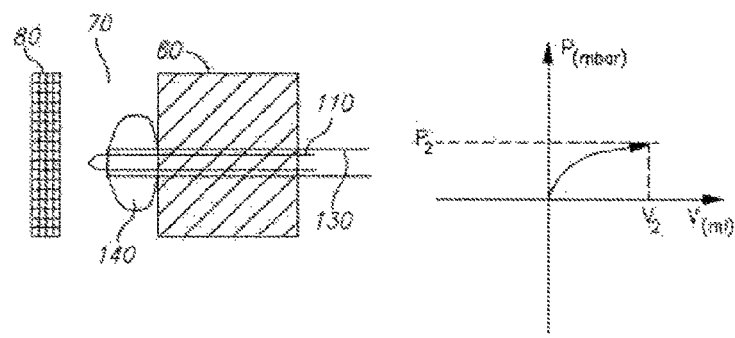
Figure 7C:
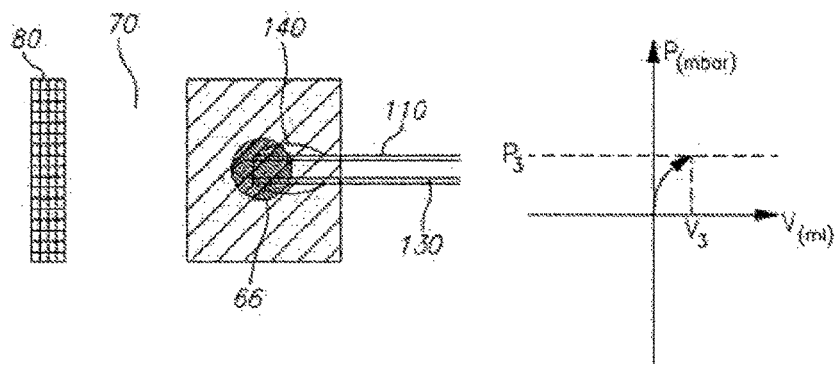

FIGS. 7A-7C are high level schematic illustrations of a behavior of sensing balloon 140 when disposed inside different tissues, as well as graphs that describe the pressure vs. volume curves of sensing balloon 140, according to some embodiments of the invention. Each figure illustrates a state of balloon 140 in the process and a corresponding inflation or deflation illustrated by graphs showing schematically the pressure level in balloon 140 and the addition or subtraction of fluid volume to balloon 140. Prior to insertion of device 100 into the body, sensing balloon 140 may be inflated to a predefined pressure, for example 10 mbar. For safety reasons and in order to avoid the risk of tissue injury, the inflation process may have preconfigured safety values such as the maximum pressure (e.g., 250 mbar) and maximum volume (e.g., 0.1 ml). These safety values may be assured by any of: expanding system 150, designed balloon strength and sealing elements 115, 116 (in embodiments comprising them).

Needle 130 with cannula 110 installed on it may be advanced through the tissues. Upon reaching ligamentum flavum 60, the pressure inside sensing balloon 140 increases due to pressure being exerted upon it by the tissue. In response to this change in pressure, microcontroller 153 may controllably empty fluid or gas out of sensing balloon 140 using pump 151 in order to maintain the predefined pressure (see an example for a pressure reduction to $p_1$ and fluid volume loss $v_1$ in the schematic graph in FIG. 7A). The volume of the fluid that is pumped out of balloon 140 and the pressure changes measured by sensor may be calculated by the microcontroller 153 to determine that ligamentum flavum 60 has been reached.

In certain embodiments, the changes in pressure and volume measured by sensor 155 in sensing balloon 140 may be processed and analyzed by microcontroller 153 using mathematical algorithms to identify the type of tissue and transitions between different tissues. According to the data, system 150 may be adjusted to detect a significant change in these characteristics during advancement of needle 130 together with cannula 110 through the different tissues. Such a change may occur upon entrance of balloon 140 into epidural space 70, which is characterized by totally different characteristics of elasticity than ligamentum flavum 60. Without being bound by theory, the natural low pressure inside epidural space 70 together with its high compliance may result in a pressure drop inside sensing balloon 140 together with a relatively significant amount of fluid or gas that may be pumped back into balloon 140 in order to maintain the predefined pressure (see an example for a pressure enhancement to $p_2$ and fluid volume increase $v_2$ in the schematic graph in FIG. 7B).

System 150 may be arranged to detect such expected reaction and indicate its occurrence. In certain embodiments, a ratio between the previous measurement (for example, the amount of fluid $v_2$ that was pumped out to maintain predefined pressure $p_2$) and current measurement is calculated. If the ratio is smaller than a predefined threshold value, it is determined that no tissue transition has occurred, and cannula 110 is advanced. If the ratio is bigger than the predefined value, it means that a tissue transition has occurred. In certain embodiments, maintaining a constant pressure throughout the process may be strived at, and then $p_1 = p_2$. In certain embodiment, specific pressure levels may be defined for each stage of the process.

Advantageously, the method copes successfully with false positive identification of epidural space 70 due e.g., to clinically well-established presence of gaps or fat pockets 66 inside ligamentum flavum 60 (see FIG. 7C) which may mislead the physician in locating the epidural space 70 by generating a pressure drop while needle 130 is still in ligamentum flavum tissue 60 (namely in a gap of fat packet 66 therein)—in case a needle passes through these gaps or pockets 66, a sudden loss of resistance may be felt by the physician that can mistakenly presume that he has reached epidural space 70. Advantageously, since sensing balloon 140 has a substantially larger volume than these gaps or fat pockets 66, it can cope successfully with these false positive identifications.

Upon entering a gap or pocket 66, the pressure measured inside sensing balloon 140 may drop and expanding mechanism 150 may pump fluid or gas into sensing balloon 140 to reach the predefined pressure (e.g., 10 mbar, see an example for a pressure enhancement to $p_3$ and fluid volume increase $v_3$ in the schematic graph in FIG. 7C). Since these gaps/fat pockets 66 are very small, the expected amount of volume necessary to reach the predefined pressure may be substantially smaller than that expected in epidural space 70, $v_3 < v_2$, thus indicating a potentially false positive detection of epidural space 70 which may be identified and avoided.

Figure 8:
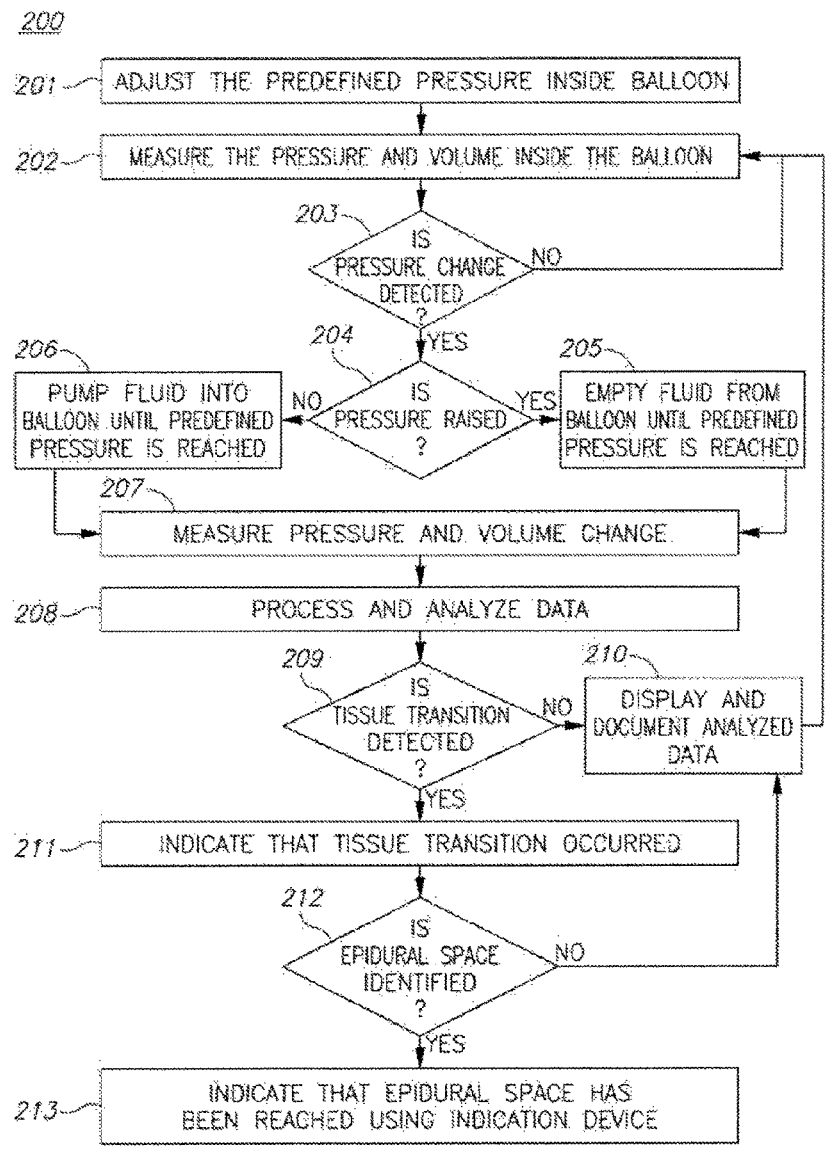
FIG. 8 is a high level schematic flow chart illustrating an exemplary method of epidural access procedure, according to some embodiments of the invention.

FIG. 8 is a high level schematic flow chart illustrating an exemplary method 200 of epidural access procedure, according to some embodiments of the invention. Method 200 starts by advancing a cannula which is installed over a needle into a mammalian tissue. In certain embodiments, method 200 may comprise using certain embodiments of device 100. Method 200 proceeds with the following steps: adjusting a predefined pressure inside a balloon attached to the cannula (step 201), e.g., by microcontroller 153 to e.g., 10 mbar, using pump 151. Measuring pressure and volume inside the balloon (step 202), e.g., continuously by sensors 155 and analyzing the measurements, e.g., by micro-controller 153. If the volume inside the balloon exceeds a preconfigured maximum safety value, pump 151 may immediately evacuate fluid or gas out of balloon 140. Method 200 then checks if a pressure change is detected (step 203). The microcontroller 153 may analyze the pressure being measured by sensor 155. If a change in pressure is detected, method 200 may proceed with step 204 (see below). If there is no change in pressure, method 200 may proceed with step 202 (see above). Since the pressure inside sensing balloon 140 is not constant and usually fluctuates due to movements inside the tissue, a pressure change may be recognized only if it exceeds preconfigured upper and lower thresholds.

In step 204, method 200 checks if the pressure inside the sensing balloon is raised. If the pressure inside the balloon is raised, method 200 may proceed with step 205 (see below). If the pressure drops, method 200 may proceed with step 206 (see below). In step 205, method 200 empties fluid from the balloon until a predefined pressure is reached. For example, microcontroller 153 may control pump 151 to empty fluid from sensing balloon 140 until the predefined pressure is being measured again inside sensing balloon 140. In step 205, method 200 pumps fluid into the balloon until a predefined pressure is reached. For example, microcontroller 153 may control pump 151 to pump fluid into sensing balloon 140 until the predefined pressure is being measured again inside balloon 140. In both cases, method 200 proceeds to step 207—measuring pressure and volume changes. For example, simultaneously to step 205 or step 206 pressure and volume sensors 155 may measure the instantaneous pressure and volume inside balloon 140 respectively.

Method 200 continues as follows: Step 208: Process and analyze data. The pressure and volume measured by the sensors are processed by the microcontroller to provide a curve of pressure vs. volume. A set of mathematical operations may be used to analyze this curve and determine the tissue type, for example, by comparing it to a known index or database. Step 209 Is tissue transition detected? If the current analyzed data is different from the previous measurement go to step 211, else go to step 210. Step 210: Display and document analyzed data; Microcontroller 153 indicates the tissue type, as well as other analyzed data (e.g., curve of pressure vs. volume) to the operator over the indication device 156. Analyzed data may be stored in the microcontroller 153 memory to document the procedure or inside extra memory 154. Such documentation is necessary for multiple purposes, such as maintaining a patient's record, research purposes or medico-legal purposes. Step 211: Indicate that tissue transition occurred; Indicate that a tissue transition has occurred using indication device 156 (e.g., acoustic or visual indication) and go to step 212. Step 212: Is Epidural Space identified? If the current analyzed data determine that epidural space 70 was detected, go to step 213, else go to step 210. Step 213: indicate that epidural space 70 has been reached using indication device 156 (e.g. acoustic or visual indication).

Figure 9:
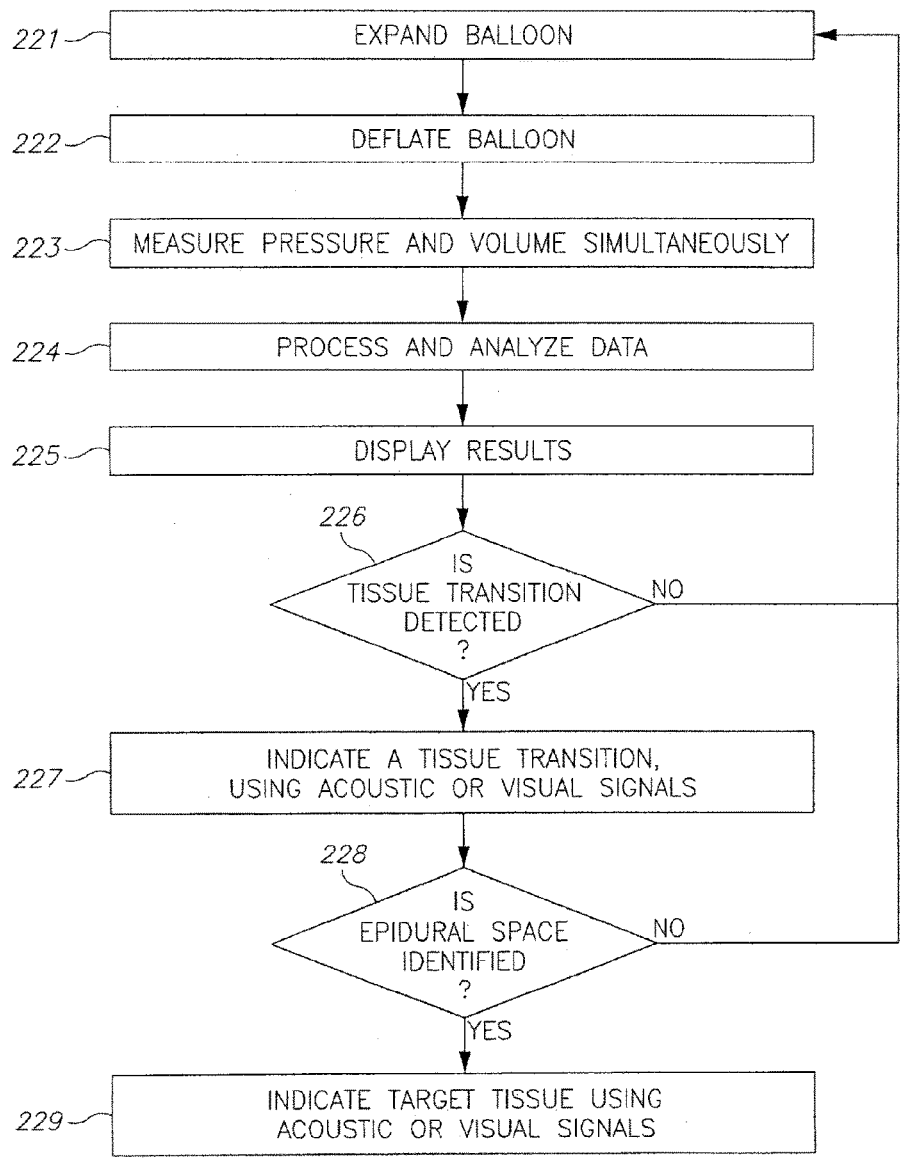
FIG. 9 is a high level schematic flow chart illustrating an exemplary method of identifying types of tissue and transitions between different tissues, according to some embodiments of the invention.

FIG. 9 is a high level schematic flow chart illustrating an exemplary method 220 of identifying types of tissue and transitions between different tissues, according to some embodiments of the invention. Method 220 starts by advancing a cannula which is installed over a needle into a mammalian tissue. In certain embodiments, method 220 may comprise using certain embodiments of device 100. Method 220 proceeds with the following steps: First, a microcontroller controls the inflation (step 221) and deflation (step 222) of a sensing balloon, the inflation and deflation are performed in order to displace the surroundings tissue (in certain embodiments to a distance of between 1-5 mm) and to extract mechanical data from the tissue surrounding the sensing balloon, which is related to and indicative of the elasticity of the surrounding tissue. For safety reasons and in order to avoid damage to the tissue engaged with the sensing balloon, the inflation process may have preconfigured safety values such as the maximum pressure (e.g., 125 mbar) and maximum volume (e.g., 0.1 ml). Steps 221 and 222, controlled by the microcontroller may be operator dependent (semi-automatic), for example they may be performed by pressing a button or a paddle, when the sensing balloon is inside an unknown tissue. Alternatively or additionally, these steps may be performed automatically in any of two ways: either by a time driven operation, meaning that the microcontroller controls the inflation and deflation of the sensing balloon automatically in preconfigured time intervals (e.g., every 0.5 seconds) and/or by an event driven operation, meaning that a change in a measured parameter of the balloon, relative to a preconfigured value, such as a pressure change or a volume change, may initiate the step of inflation and deflation of the balloon inside the surrounding tissue by the microcontroller. In case step 221 is triggered by a pressure change and/or volume from the preconfigured value, step 222 will deflate balloon 140 back to its preconfigured value in order to enable further measurements.

Method 220 continues as follows: pressure and volume inside the sensing balloon are measured (step 223), e.g., by pressure and volume sensors 155, during the expansion and contraction of the sensing balloon. The pressure of the sensing balloon per a specific volume reflects the mechanical properties of the tissues engaged with the sensing balloon and may be analyzed by the microcontroller and compared to a known index (step 224) to determining the type of tissue engaged by the sensing balloon and transitions between different tissues. The type of tissue engaged by the sensing balloon may be displayed on indication device 156 (step 225). Additionally, other analyzed data, such as pressure vs. volume curve and timeline may be displayed. Once a tissue is identified, the microcontroller may compare it to the previous measure (step 226) to indicate with visual and acoustic signals if a transition between tissues has occurred (step 227). Thereafter, if epidural space 70 has been reached (step 228), visual and acoustic signals may be given (step 229).

In certain embodiments, data measured by pressure and volume sensors 155 during expansion and contraction of sensing balloon 140, may be stored by microcontroller 153. The measured data may be processed by microcontroller 153 to produce a set of data curves. This set of curves may comprise, for example, a P/V curve (pressure changes vs. volume changes or vice versa), P/T curve (pressure vs. time or vice versa) or V/T curve (volume vs. time or vice versa). These sets of curves contain data that may indicate the mechanical properties (e.g., elasticity) of a tissue, and may be further processed by microcontroller 153 using a set of mathematical operations to facilitate determining the type of tissue engaged with sensing balloon 140 and transition between different tissues. The mathematical operations that may be calculated for analyzing the data are, for example, an integral of the P/V curves or the slope of the P/V curves along several segments.

Figure 10:
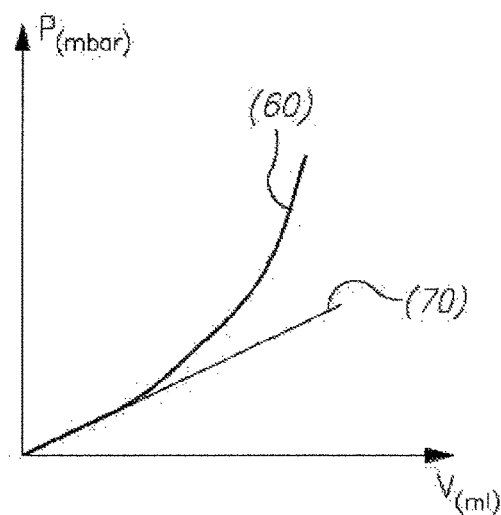
FIG. 10 is a high level schematic illustration of an exemplary pressure vs. volume curve that may be obtained by a sensing balloon, according to some embodiments of the invention.

FIG. 10 is a high level schematic illustration of an exemplary pressure vs. volume curve that may be obtained by sensing balloon 140, according to some embodiments of the invention. Curve 60 represents the pressure to volume measurements with sensing balloon 140 positioned inside ligamentum flavum 60, while curve 70 represents the pressure to volume measurements with sensing balloon 140 positioned inside epidural space 70 and is being expanded to a preconfigured volume or pressure. The P/V curve of ligamentum flavum 60 demonstrates a non-linear spring behavior, which is typical to this extremely elastic tissue. The integral value of the P/V curve when balloon 140 is disposed inside ligamentum flavum 60 in comparison to the integral value of the P/V curve when balloon 140 is disposed inside epidural space 70 reflects the differentiation between these two different tissue types. An advantage of using this mathematical operation is in minimizing the weight of a few biased measurement points that can erroneously be measured. Another advantage is that this mathematical operation may assist in determining type of tissue when absolute measurement points are insufficient to determine the tissue type.

Another method to identify tissues type and transitions between different tissues according to certain embodiments is performed using the following steps: needle 130 with cannula 110 installed on it may be inserted into the ligaments while sensing balloon 140 is in vacuum state. Then, balloon 140 may be inflated to a predefined volume, for example 0.05 ml, and the pressure inside it may be measured by pressure sensor 155. Such measurement may assist in defining the elasticity characteristics of the tissue (relating e.g., to a respective patient). According to the data, system 150 may be adjusted to detect a significant change in these characteristics during advancement of needle 130 together with cannula 110. Upon reaching epidural space 70, a significant drop of pressure may occur, indicating successful penetration into epidural space 70.

Figure 11:
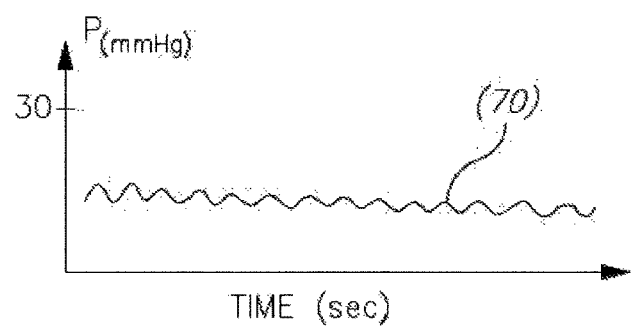
FIG. 11 is a high level schematic illustration of an exemplary EPWF curve that may be obtained by a sensing balloon, according to some embodiments of the invention.

In certain embodiments, ambient pressure and pressure pulsation of anatomical structure that are engaged with sensing balloon 140 may be to continuously measured and analyzed. These measurements have a major advantage for safety reasons as they may assist in identifying structures that are important for the success and safety of various procedures carried out in various tissues. Two examples for pressure pulsations are blood pulsation inside blood vessels and epidural pressure waveform (EPWF). The latter is a unique pressure waveform generated inside epidural space 70. FIG. 11 is a high level schematic illustration of an exemplary EPWF curve that may be obtained by sensing balloon 140, according to some embodiments of the invention. Without being bound to theory, EPWF may have amplitude of about 13 mbar and is considered a sensitive marker to detect epidural space 70. In clinical literature, a method of measuring the EPWF was demonstrated by continuous administration of fluid into the epidural space and measurement of the rapid changes in pressure. This method has a disadvantage as it changes the ambient pressure of the anatomical structure (the epidural space for example) and since it is hard to maintain such a continuous measurement. Another disadvantage of this method is that it exposes the patient to a potential risk of contamination, due to the fluid that should be spread inside epidural space 70. Advantageously, in comparison to the prior art, certain embodiments of the present invention enable a continuous measurement of the pressure pulsation, while reducing or even eliminating the need to administrate fluids or gas.

The method of continuously measures and analyzes ambient pressure and pressure pulsation of the anatomical structure engaged with sensing balloon 140 comprises several steps: First, sensing balloon 140 is inflated to a predefined volume. The balloon is engaged with the anatomical structure which exerts pressure pulsation on sensing balloon 140. Next, pressure sensor 155 measures the rapid changes in pressure inside the sensing balloon 140. The measured data is stored in microcontroller 153 and analyzed to detect the frequency of the pulsation. The data is analyzed by mathematical operations known in the prior art such as fast furrier transform (FFT). After the data is analyzed, it may be compared to a known index to identify the anatomical structure. The analyzed data may be shown to the user by visual or acoustic means in the indication device 156 (For example the frequency of the pulsation may be shown on a small LCD screen).

During an epidural access procedure, once inflated inside epidural space 70, sensing balloon 140 may be able to detect the EPWF, which is considered a sensitive marker for a correct placement of epidural needle, and thereby reduce the risk of misplacement of device 100 tremendously. In addition, sensing balloon 140 may be arranged to perform a continuous monitoring of the EPWF as long as cannula 110 is inside epidural space 70. Such monitoring may be advantageous to overcome the common problems of undetected catheter migration, which may result in failure of the patient analgesia or anesthesia. During the continuous stage, the EPWF may be monitored to ensure that cannula 110 is well positioned inside epidural space 70. In case the EPWF disappears, an alert may be given to the patient or physician to notify them that cannula 110 has migrated outside of epidural space 70. In certain embodiments, the monitoring of EPWF using sensing balloon 140 may be a feature of devices other than expanding mechanism 150. For example, it may be performed by connecting cannula 110 to a patient controlled analgesia (PCA) pump having a pressure sensor. Such devices are hence to be understood as certain embodiments of the present invention.

Figure 12:
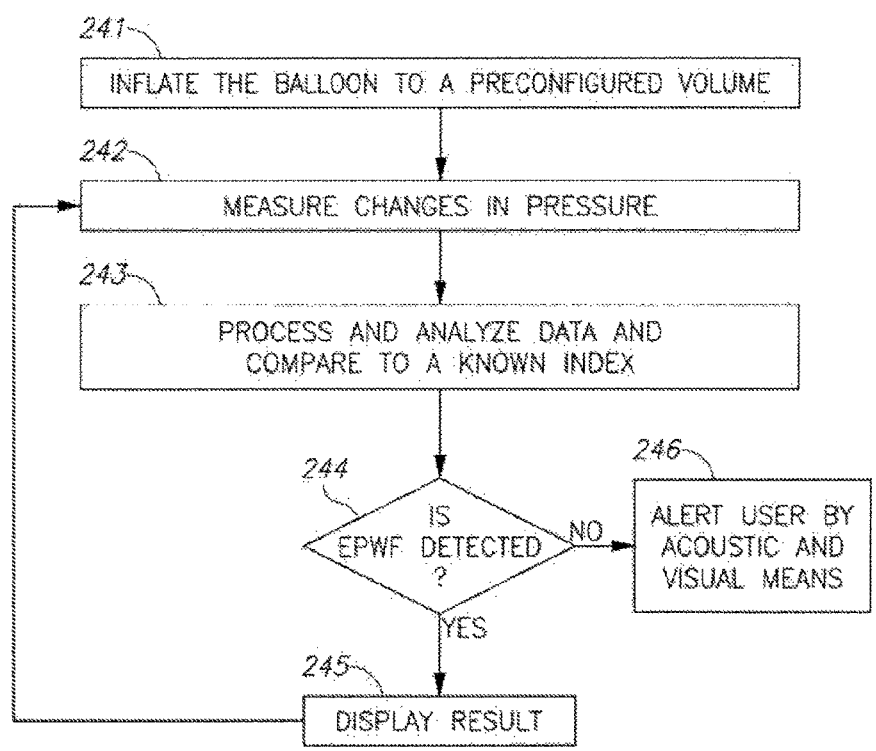
FIG. 12 is a high level schematic flow chart illustrating an exemplary method of measuring and identifying an epidural pressure waveform (EPWF), according to some embodiments of the invention.

FIG. 12 is a high level schematic flow chart illustrating an exemplary method 240 of measuring and identifying an epidural pressure waveform (EPWF), according to some embodiments of the invention. Method 240 may be used as a complementary method to the epidural anesthesia procedure to continuously detect epidural space 70 and to alert the physician when cannula 110 migrated outside of the epidural space, for example into a paraspinal muscle or into the subarachnoid space.

Method 240 may proceeds according to the following steps:

Step 241: Inflate the balloon to a preconfigured volume: The operator inflates the balloon to a predefined volume using pump 151 and controlled by the microcontroller 153

Step 242: Measure changes in pressure: Rapid changes in the sensing balloon 140 are measured by the sensor 155 and stored in the microprocessor.

Step 243: Process and analyze data: The microprocessor analyzes the pressure measurement to determine the frequency of the pressure wave (e.g., using FFT calculation). The analyzed data is compared to a known index to conclude if cannula 110 is in epidural Space 70 or not. Other unique pressure frequencies may be measured if sensing balloon 140 is engaged in other anatomical structures such as the subarachnoid space or a blood vessel.

Step 244: Is EPWF detected?: If the unique Epidural waveform is detected go to step 245. If no pressure waveform is detected go to step 246.

Step 245: Display results: Visual and acoustic means indicate the physician that cannula 110 is in epidural space 70.

Step 246: Alert user by acoustic and visual means: Visual and acoustic means indicate the physician that cannula 110 has migrated outside epidural Space 70.

FIGS. 13A-13E are schematically illustrated cross sectional views of the stages of an epidural access procedure, according to some embodiments of the invention, including the penetration of ligamentum flavum 60 and including entering into epidural space 70.

Figures 1B, 1C, 1D, 1E:
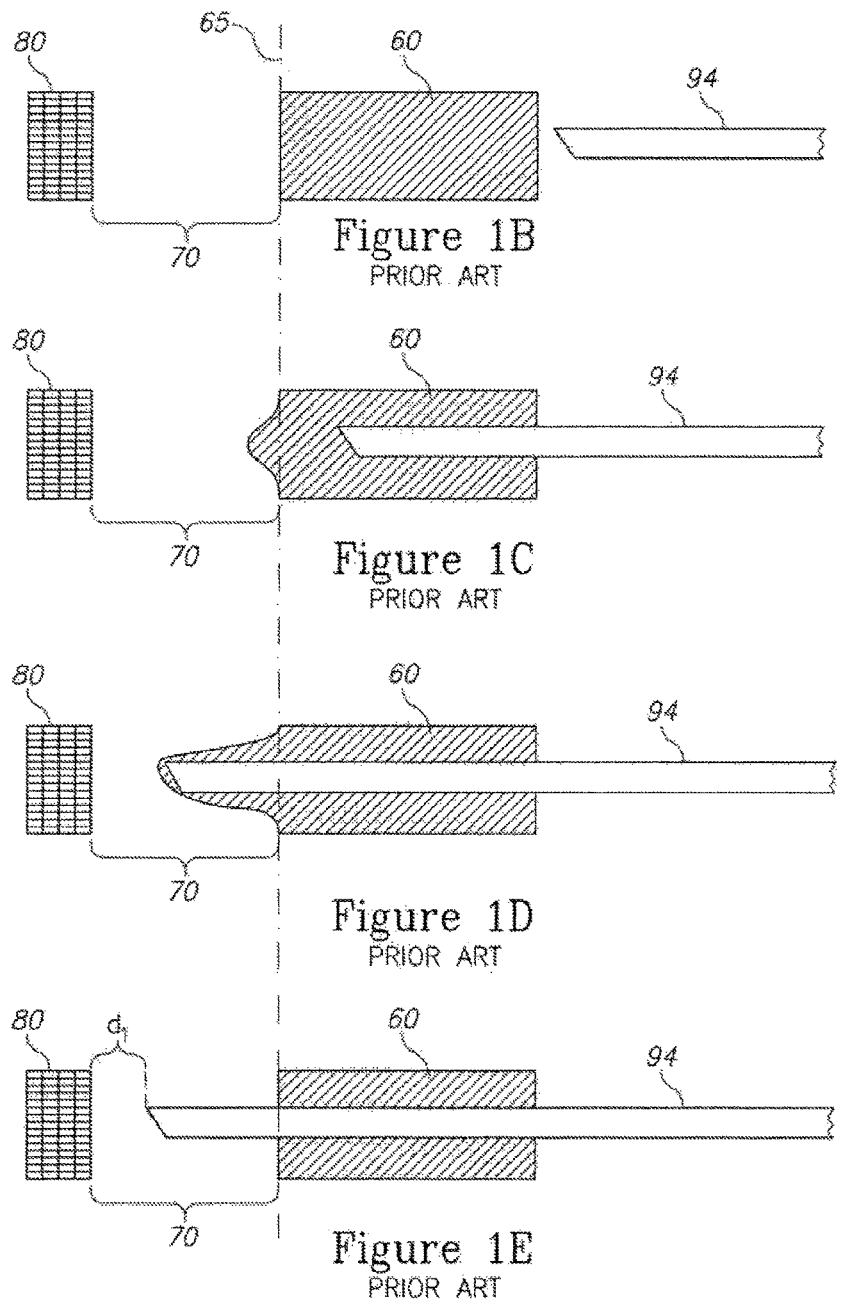
FIGS. 1B-1E are schematically illustrated cross sectional views of the stages of a typical epidural access procedure, according to the prior art.
Figure 13A:
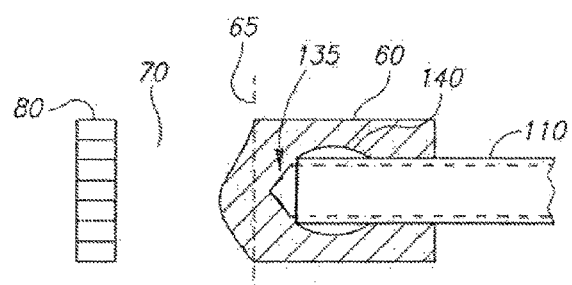
FIGS. 13A-13E are schematically illustrated cross sectional views of the stages of an epidural access procedure, according to some embodiments of the invention.
Figure 13B:
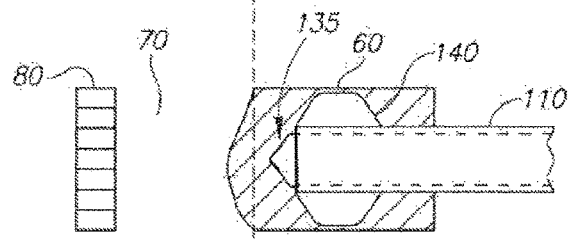
Figure 13C:
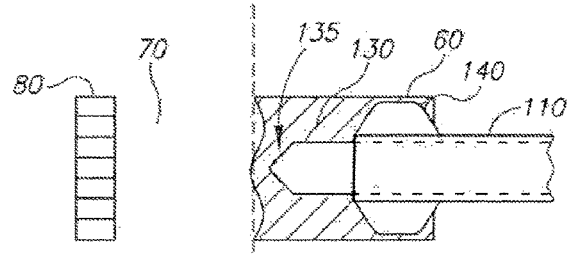
Figure 13D:
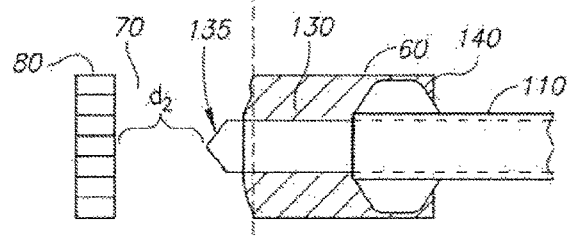
Figure 13E:
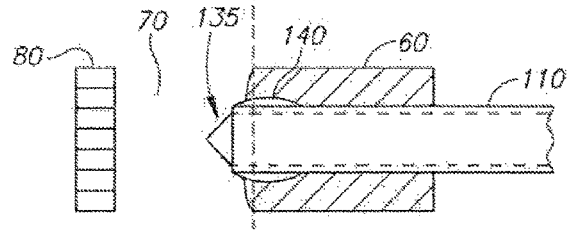

In certain embodiments a method is provided of advancing an elongated instrument such as needle 130 accurately to a preconfigured in-vivo location, for example, into epidural space 70, in an epidural access (block) procedure. The described methods are not limited to epidural access procedures, and may be used in any kind of procedure wherein an accurate penetration with reduced overshooting is required. Since, overshooting of tip 135 of needle 130 beyond epidural space 70 may puncture dura mater 80, it would be advantageous to have a procedure that substantially reduces the risk of tip 135 of needle 130 puncturing dura mater 80. Certain embodiments provide a method of erupting ligamentum flavum 60, such that needle 130 is inside epidural space 70 at a distance $d_2$ from dura mater 80, wherein distance $d_2$ is substantially larger than distance $d_1$: $d_2 \gg d_1$ (see FIG. 13D compared with FIG. 1E). Certain embodiments of the following tissue-fixation method are designed for penetrating such elastic tissues.

Without being bound to theory, a central idea behind the various tissue-fixation methods is to anchor ligamentum flavum 60 using an expandable device such as balloon 140B in order to maintain the current position of ligamentum flavum 60, thus preventing it from being pushed towards epidural space 70 as a result of advancement of needle 130 through ligamentum flavum 60.

In certain embodiments, tissue fixation device 100 comprises cannula 110 having tissue anchoring balloon 140 securely attached to the external circumference of cannula 110, proximal to distal tip 105 of cannula 110. Cannula 110 may be connected to expanding mechanism 150 or to a simple manual syringe for manually expanding and contracting balloon 140. Balloon 140 may function not only as a tissue anchoring balloon, but also for sensing the engaged tissue in order to facilitate determining the type of engaged tissue (see above). In certain embodiments (e.g., FIGS. 3B, 5D and 5E), cannula 110 may be a double balloon cannula, wherein distal sensing balloon 140A is responsible for detecting the type of the engaged tissue, while tissue anchoring balloon 140B is responsible for fixating the engaged tissue as part of the tissue-fixation method to prevent overshooting of needle 130. Cannula 110 facilitates the insertion of a sharp object, preferably a small gauge needle. In certain embodiments, it may be designed to facilitate any type of sharp object required for the penetration of an elastic tissue, such as a trocar, a Veress needle or any other sharp object. In a procedure for accessing epidural space 70, cannula 110 may facilitate an epidural needle, for example a Tuohy needle.

FIG. 4 is a high level schematic illustration of device 100 having an incremental advancing mechanism 129, according to some embodiments of the invention. Advancing mechanism 129 comprises a cannula-incremental-advancing-mechanism 124 and a needle-incremental-advancing-mechanism 125, which are located inside housing 126 arranged to secure cannula 110 and needle 130. Incremental advancing mechanisms 124 and 125 are arranged to enable incrementally advancing, in a controlled manner, of cannula 110 and needle 130 with respect to each other. The incremental advancing mechanisms may be embodied in ways know in the art, such as a screw based mechanism having threads with a preconfigured pitch of between 0.5-2 mm, a step motor etc. Housing 126 may further comprise wings 119. The operator of device 100 may push wings 119 to facilitate the advancement of device 100 through the tissues.

In certain embodiments, several expandable elements 140 such as balloons 140 may be used for anchoring the tissue before being pulled backwards. In certain embodiments, device 100 may be used for preventing needle overshoot during a procedure of epidural anesthesia as well as for preventing overshoot during other invasive procedures, such as peripheral blocks, laparoscopic surgeries, dental procedures, vascular procedures, urological procedures etc.

Figure 14:
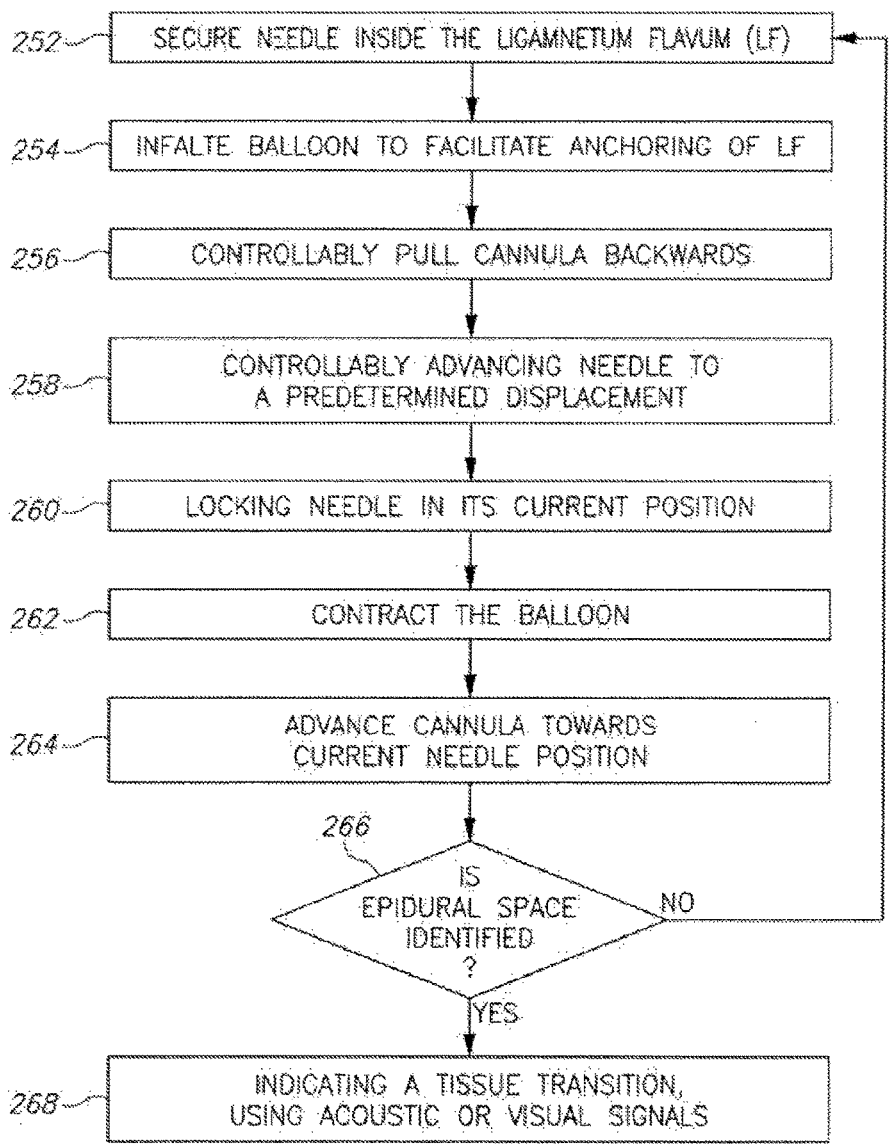
FIG. 14 is a high level schematic flow chart illustrating a non-limiting exemplary method of safely advancing a needle into the epidural space, during an epidural access procedure, according to some embodiments of the invention.

FIG. 14 is a high level schematic flow chart illustrating a non-limiting exemplary method 250 of safely advancing a needle 130 into epidural space 70, during an epidural access procedure, according to some embodiments of the invention. Method 250 is exemplified in a non-limiting manner by using device 100 to perform an epidural access procedure, but may be likewise applicable to other devices and other procedures, as explained above. Method 250 may begin by administrating needle 130 and cannula 110 of device 100 into a mammalian tissue. Method 250 may proceed with the following steps: Step 252: securing needle 130, containing balloon 140B, in ligamentum flavum 60. Needle 130 together with cannula 110 are advanced into ligamentum Flavum 60 after departing from interspinous ligament 52 (see FIGS. 1A and 13A). The operator of device 100 secures needle 130, containing balloon 140B, in ligamentum flavum 60, ligamentum flavum 60 being an elastic tissue, for example using needle-incremental-advancing-mechanism 125. The elastic tissue stretches slightly beyond the original, undistorted position. Step 254: inflating balloon 140B to facilitate anchoring of ligamentum flavum 60. The operator activates expanding mechanism 150 and thereby, balloon 140B expands and engages with ligamentum flavum 60 to facilitate strong anchoring of the tissue surrounding needle tip 135 (see FIG. 13B). Alternatively, balloon 140B may be expanded manually using a syringe. Optionally (step 256), the operator may controllably pull cannula 110 backwards to enhance anchoring. For example, using cannula-incremental-advancing-mechanism 124 illustrated in FIG. 4, the operator pulls cannula 110 backwards in order to further stretch ligamentum flavum 60 towards interspinous ligament 52, before advancing needle 130 through ligamentum flavum 60 (see FIG. 13C). Optionally, step 256 facilitates the penetration of ligamentum flavum 60 by needle 130, since pulling back ligamentum flavum 60 may help needle 130 to penetrate it while needle 130 remains static. Additionally or alternatively, method 250 may further comprise step 258: controllably advancing needle 130 to a predetermined displacement. The operator advances needle 130, e.g., using needle-incremental-advancing-mechanism 125 (FIG. 4), to a predetermined displacement, preferably 0.5-3 mm (see FIG. 13D), while balloon 140B is steadily expanded and static inside ligamentum flavum 60. Thereby, overshoot of ligamentum flavum 60 towards epidural space 70 reduces significantly due to the fixation of ligamentum flavum 60 using balloon 140B.

Method 250 may comprise the following steps. Step 260: locking needle 130 in its current position. Locking needle 130 in position, using needle-incremental-advancing-mechanism 125. Optionally, the operator may use the loss of resistance technique (LORT) to check if epidural space 70 has been reached, and then thread an epidural catheter through needle 130 to a distance of between 1-8 cm inside epidural space. Step 262: contracting balloon 140B. The operator contracts balloon 140B. The contraction may be performed in a controllable manner using expanding mechanism 150, or manually be the operator. Step 264: advancing cannula 110 towards current needle position. Cannula 110 is advanced towards needle tip 135, so that balloon 140B is close to needle tip 135 (see FIG. 13E). Step 266: check if epidural space 70 identified. The operator uses either the loss of resistance technique or balloon 140B to check if needle 130 has entered epidural space 70 (step 266). In certain embodiments, sensing balloon 140 may be used to determine whether epidural space 70 has been reached. If epidural space 70 is not identified, but rather that ligamentum flavum 60 is still identified, go to step 252. Optionally, method 250 may further comprise step 268: indicating a tissue transition, using acoustic or visual signal. An indicator may be arranged to indicate a tissue transition event (from ligamentum flavum 60 to epidural space 70), using an acoustic, visual or any other indicatory signal.

Figure 15:
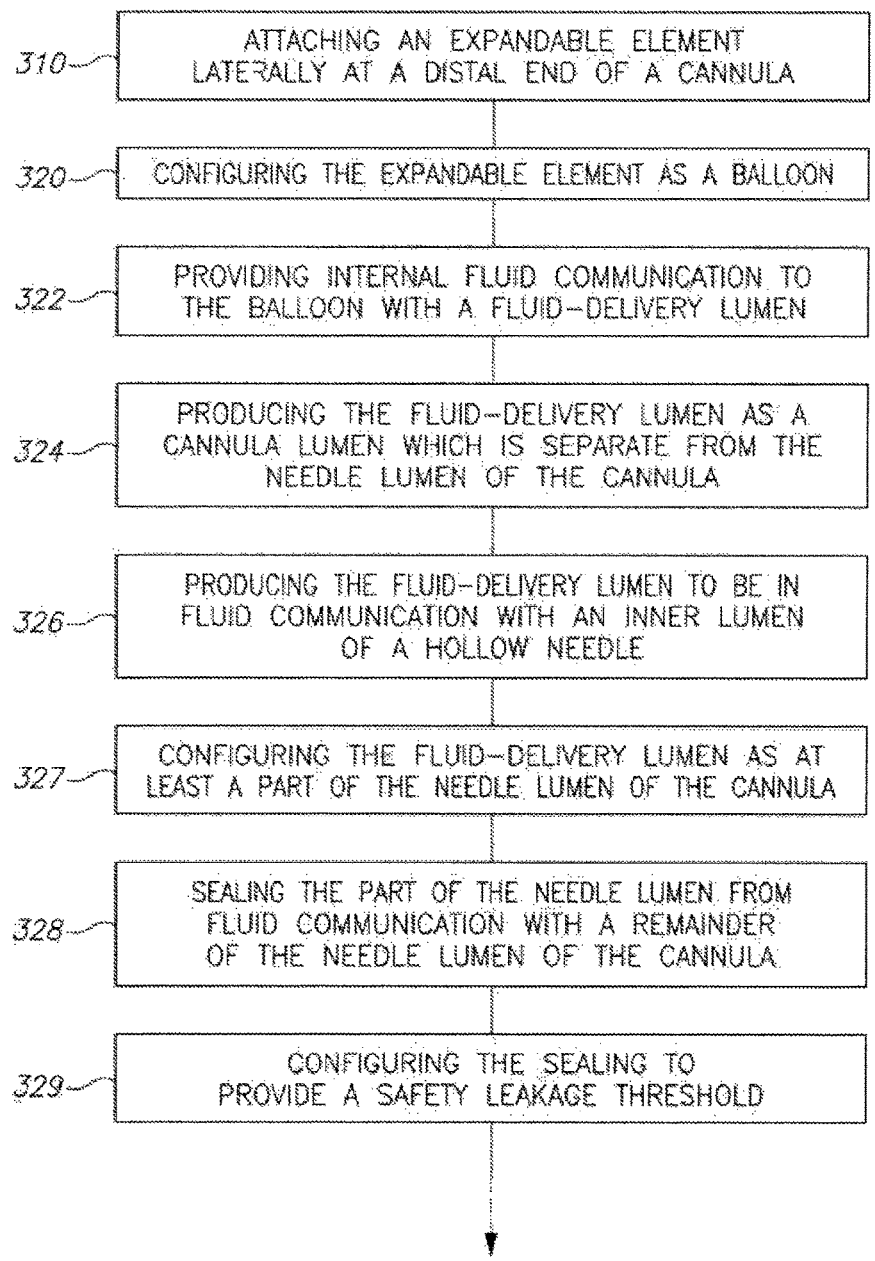
FIGS. 15 and 16 are high level schematic flow charts illustrating methods, according to some embodiments of the invention.
Figure 16:
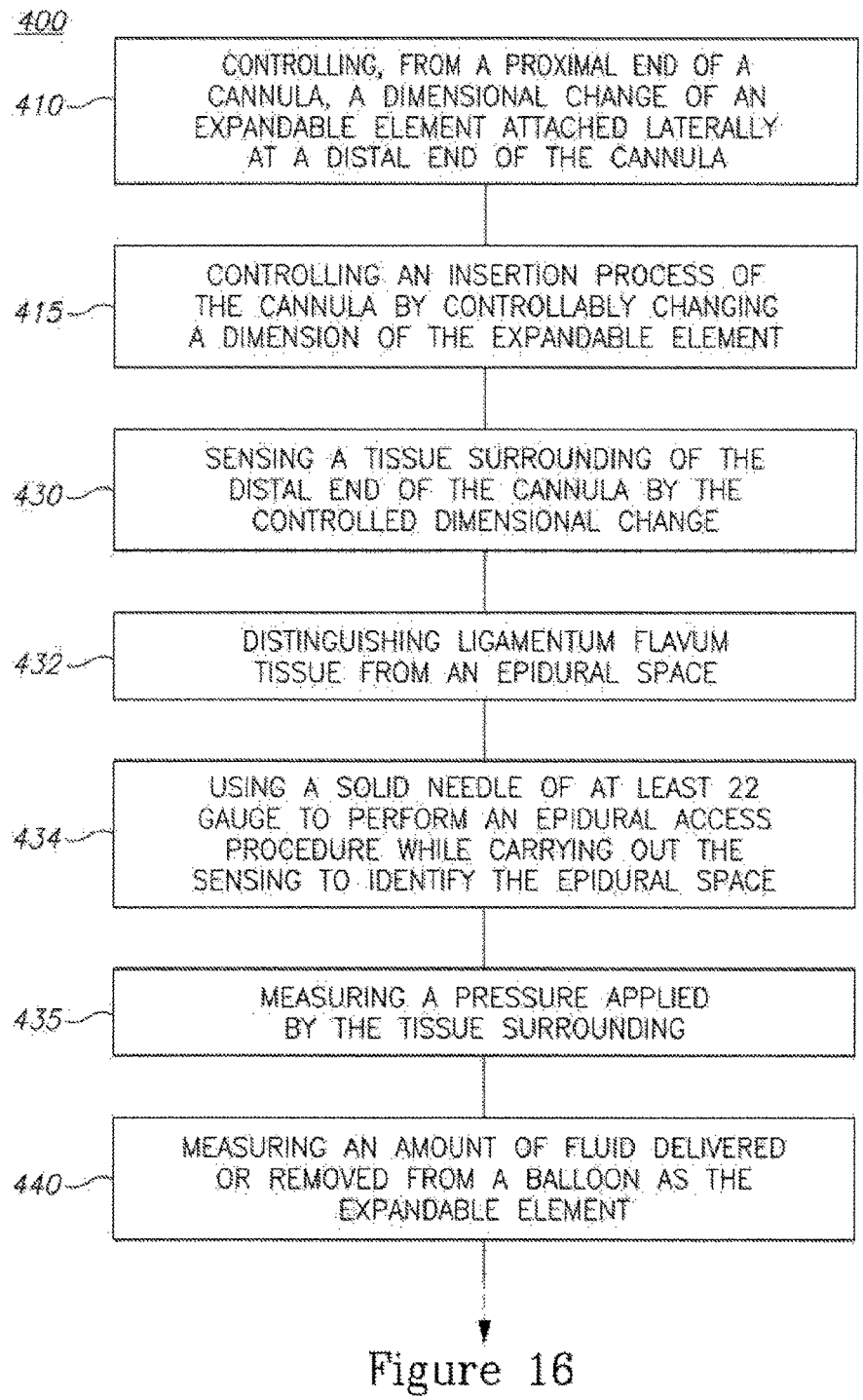

FIGS. 15 and 16 are high level schematic flow charts illustrating methods 300 and 400, respectively, according to some embodiments of the invention.

Method 300 comprises attaching an expandable element laterally at a distal end of a cannula (stage 310), the cannula having a needle movable therethrough in a needle lumen of the cannula, and controlling a dimensional change of the expandable element from a proximal end of the cannula (stage 370). In certain embodiments, method 300 further comprises configuring the expandable element as a balloon (stage 320), providing internal fluid communication to the balloon with a fluid-delivery lumen (stage 322), and configuring the balloon to be expandable by introduction of a fluid through the fluid-delivery lumen (stage 340).

In certain embodiments, method 300 further comprises producing the fluid-delivery lumen as a cannula lumen which is separate from the needle lumen of the cannula (stage 324). In certain embodiments, method 300 further comprises producing the fluid-delivery lumen to be in fluid communication with an inner lumen of a hollow needle (stage 326). In certain embodiments, the fluid-delivery lumen is at least a part of the needle lumen of the cannula (stage 327) and method 300 further comprises sealing the part of the needle lumen from fluid communication with a remainder of the needle lumen of the cannula (stage 328) and optionally configuring the sealing to provide a safety leakage threshold (stage 329).

In certain embodiments, method 300 further comprises attaching the balloon on the distal end of the cannula (stage 342) and/or attaching the balloon at a specified distance from the distal end of the cannula (stage 344). In certain embodiments, method 300 further comprises configuring the balloon to be circumferential (stage 346) and optionally attaching an anchoring element to the cannula, proximally to the expandable element (stage 350). In certain embodiments, method 300 further comprises configuring the anchoring element as a balloon (stage 352), providing internal fluid communication to the balloon with a fluid-delivery lumen (stage 322) and configuring the balloon to be expandable by introduction of a fluid through the fluid-delivery lumen (stage 340).

In certain embodiments, method 300 further comprises controlling the dimensional change of the expandable element (stage 370) and/or measuring a pressure applied onto the expandable element (stage 380). In certain embodiments, the expandable element is a sensing balloon which is internally in fluid communication with a fluid-delivery lumen and is expandable by introduction of a fluid therethrough. In certain embodiments, method 300 further comprises measuring a pressure applied onto the sensing balloon by measuring amounts of fluid required to maintain a constant pressure in the sensing balloon during a movement thereof through tissue (stage 382).

In certain embodiments, method 300 further comprises measuring a tissue response by at least one of inflating and deflating the sensing balloon controllably (stage 385) and in certain embodiments measuring the tissue response periodically or upon manual prompting (stage 387). In certain embodiments, method 300 further comprises measuring a pressure applied onto the sensing balloon and further comprising measuring the tissue response upon measuring at least one pressure threshold (stage 389).

In certain embodiments, method 300 further comprises distinguishing, according to the measured tissue response, ligamentum flavum tissue from an epidural space (stage 390). In certain embodiments, method 300 further comprises identifying, according to the measured tissue response, an epidural pressure waveform, indicative of a position of the sensing balloon with an epidural space (stage 395).

In certain embodiments, method 300 further comprises configuring the expandable element as an anchoring balloon and producing the anchoring balloon either on the distal end of the cannula or at a specified distance from the distal end of the cannula (stage 354), selected to anchor the anchoring balloon in ligamentum flavum tissue with a cannula tip protruding into an epidural space (stage 356).

In certain embodiments, method 300 further comprises configuring a cannula tip to resist deformation upon introduction of the cannula into tissue (stage 360). In certain embodiments, method 300 further comprises configuring the expandable element to be mechanically expandable (stage 365). In certain embodiments, method 300 further comprises pre-forming the expandable element from a shape memory alloy (stage 367).

Method 400 (FIG. 16) comprises controlling, from a proximal end of a cannula, a dimensional change of an expandable element attached laterally at a distal end of the cannula (stage 410). For example, method 400 may comprise controlling an insertion process of the cannula by controllably changing at least one dimension of the expandable element (stage 415). In certain embodiments, method 400 may comprise distinguishing ligamentum flavum tissue from an epidural space (stage 432).

In certain embodiments, method 400 further comprises sensing a tissue surrounding of the distal end of the cannula by the controlled dimensional change (stage 430), e.g., the sensing may be carried out to identify the epidural space (stage 434). In certain embodiments, method 400 may comprise measuring an amount of fluid delivered or removed from a balloon as the expandable element (stage 440).

In certain embodiments, method 400 may comprise using a solid needle of at least 22 gauge to perform an epidural access procedure while measuring a pressure applied by the tissue surrounding (stage 435).

In certain embodiments, method 400 may comprise carrying out the controlled dimensional change periodically, upon manual actuation and/or upon an automatic actuation related to a sensing result (stage 450).

In certain embodiments, method 400 further comprises anchoring the distal end of the cannula by the expandable element (stage 470), for example anchoring the cannula at ligamentum flavum tissue or within the epidural space (stage 472). In certain embodiments, method 400 comprises using the cannula as a catheter or inserting a catheter through the cannula (stage 490).

The distance of sensing balloon 140 from tip 135 of needle 130 should be minimal so that balloon 140 will sense the tissue that surrounds tip 135 of needle 130.

Figure 17A:
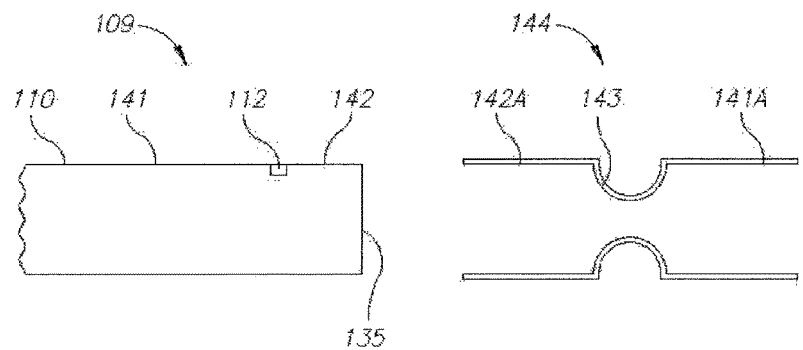
FIGS. 17A-17K are high level schematic illustrations of configurations and attachment methods of a balloon to a cannula or a needle distally, according to some embodiments of the invention.
Figure 17B:
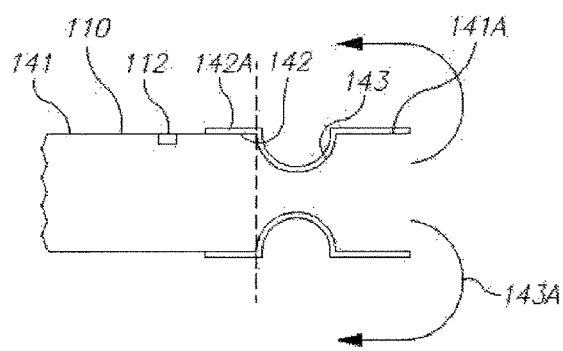
Figure 17C:
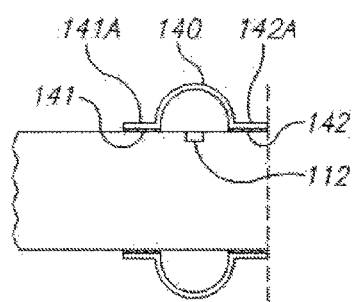

FIGS. 17A-17C are high level schematic illustrations of an attachment method of balloon 140 to cannula 110, according to some embodiments of the invention. This method enables the positioning of balloon 140 right at the tip 105 of cannula 110. Cannula 110 may comprise proximal and distal attachment regions 141, 142 (respectively) at distal end 109 thereof, on either side of opening 112 (for inflating and deflating balloon 140). Balloon 140 may be produced, for example, using a balloon blow molding process, wherein a tube or a sleeve is deformed to become a balloon. Balloon 140 is comprised of proximal neck 141A, distal neck 142A and expanding member 143 in between. An attachment process may comprise attaching distal neck 142A to a more distal cannula attachment region 142, which may be positioned at the very tip 105 of cannula 110 (FIG. 17B), and then turning balloon 140 inside out (arrow 143A) to attach proximal neck 141A to the other cannula attachment region 141, on the other side of opening 112 (FIG. 17C). This production process brings expanding member 143 in front of opening 112 to define internal lumen 122A of balloon 140. Attachment of necks 141A and 142A to cannula may be done using various methods known in the art, such as thermal bonding, gluing (with UV or other glues), RF welding etc.

In certain embodiments, the attachment method may be applied to any expandable element 140. Cannula 110 may comprise at least a distal and a proximal attachment regions at either side of distal cannula opening 112. Expandable element 140 may comprise a sleeve having at least two respective attachment regions at either side thereof, one respective attachment region attachable to the distal cannula attachment region and another respective attachment region attachable to the proximal cannula attachment region after turning the sleeve inside out, to place expandable member 140 in proximity to distal cannula opening 112. The distal cannula attachment region may be within 1 mm of cannula tip 105. Method 300 may further comprise attaching the expandable element to a distal cannula tip and turning the expandable element inside out over the cannula tip.

Figure 17D:
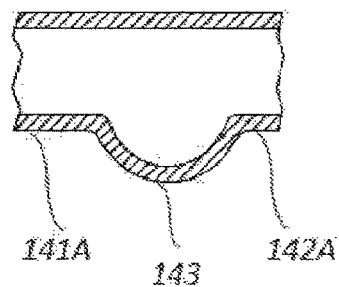
Figure 17E:
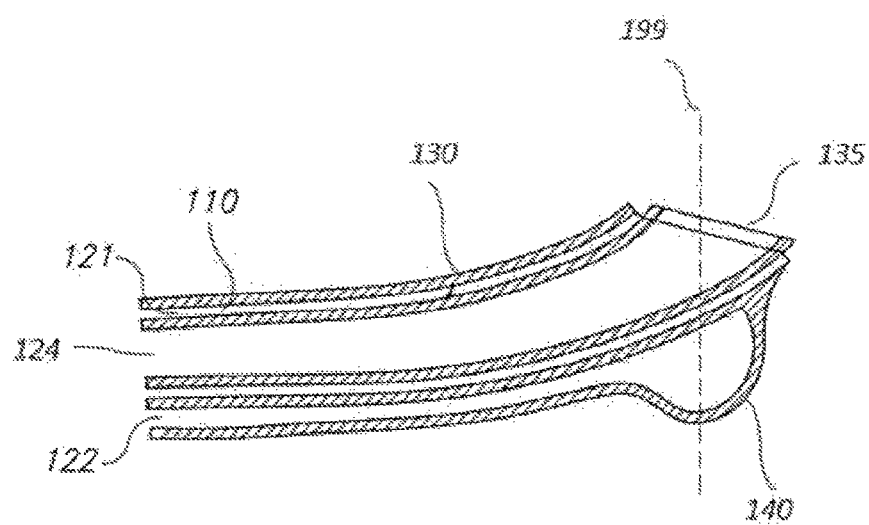
Figure 17J:
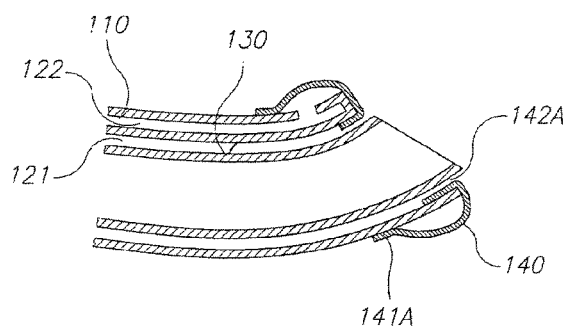
Figure 17K:
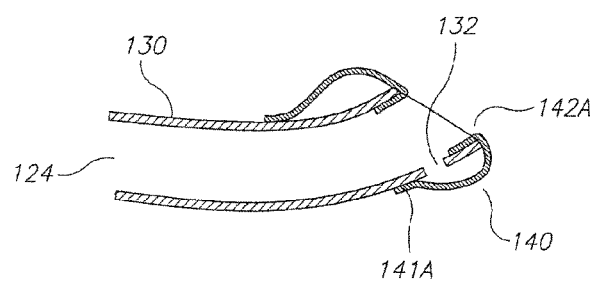
Figure 18A:
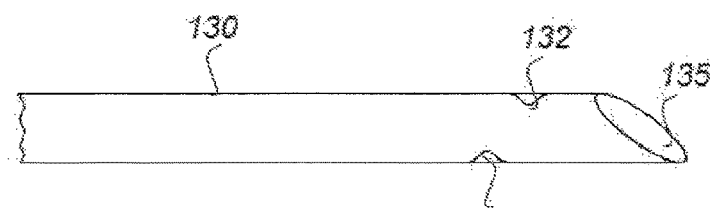
FIGS. 18A-D are high level schematic illustrations of a device comprising a sensing balloon that is attached directly to a needle and a stylet that directs fluid into the balloon, according to some embodiments of the invention.
Figure 18B:
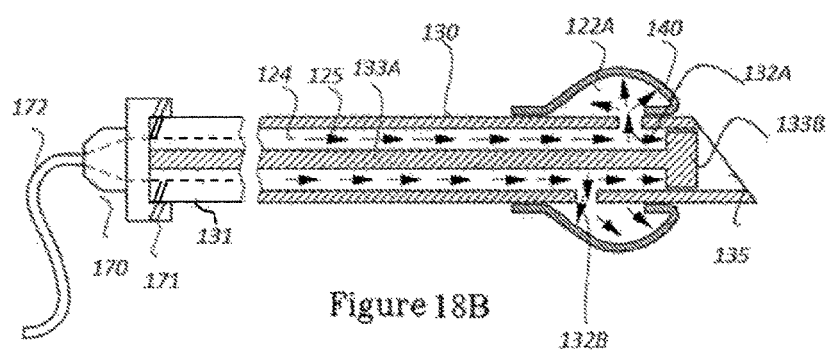
Figure 18C:
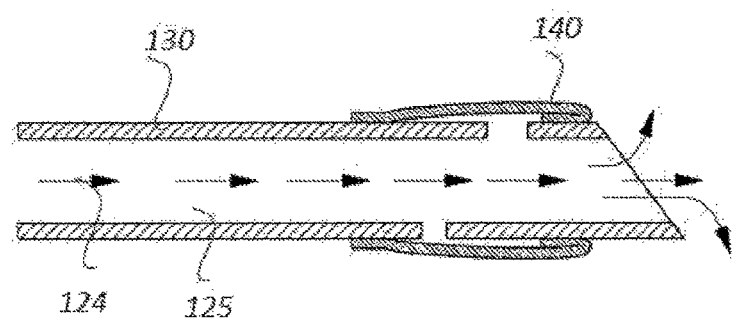
Figure 18D:
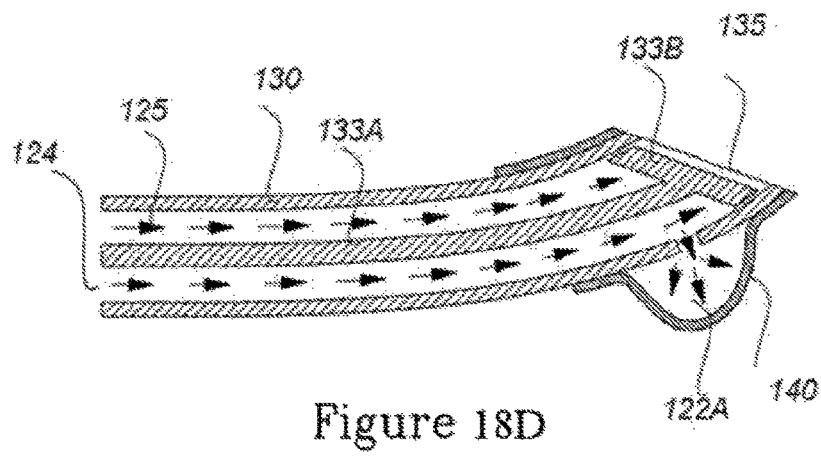

In certain embodiments, balloon 140 may be designed as a drop-like balloon 140 (partly circumferential) at cannula tip 105 or needle tip 135 as illustrated in FIGS. 17E and 18D respectively. Balloon 140 can be blow molded directly from cannula 110 (FIG. 17E), thus saving the need to bond the balloon. Such process may involve a co-extruded cannula, wherein the part of cannula that is blow molded to a balloon is made of a softer material than the rest of the cannula. Balloon 140 may also be manufactured separately, using, for instance, a sleeve that is blow molded to a partly circumferential balloon (FIG. 17D), and then bonding it to the outer circumference of tip 105 or tip 135. In another embodiment, distal neck 142A of balloon 140 is bonded inside the inner walls of tip 105 of cannula 100 or inside the inner walls of tip 135 of needle 130 (FIGS. 17J and 17K)

The type of needle 130 being used affects the optimal positioning of sensing balloon 140 closer to tip 135. In one embodiment, a "Tuohy" needle 130 having a curved tip is being used (FIG. 17E), so that the positioning of a drop-like balloon 140 right on the curve of needle 130 enables the centers of both balloon 140 and the opening of needle 130 to be aligned along the same imaginary dashed line 199. In another embodiment, needle 130 may be a pencil-point needle, such as a "Sprotte" needle, that enables balloon formation as close as 1 mm from needle tip 135 due to its symmetrical nature.

Figure 17F:
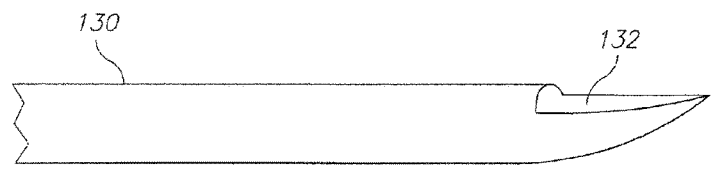
Figure 17G:
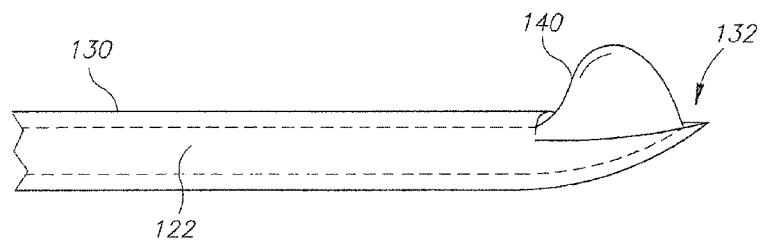
Figure 17H:
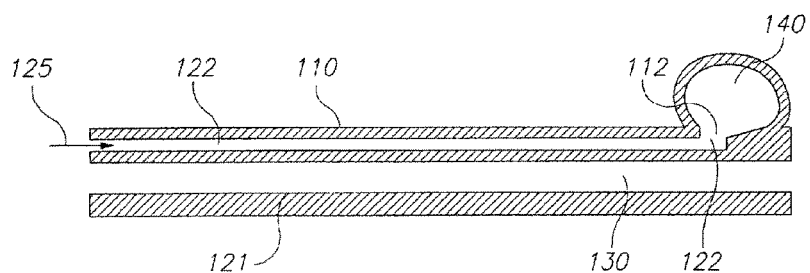
Figure 17I:
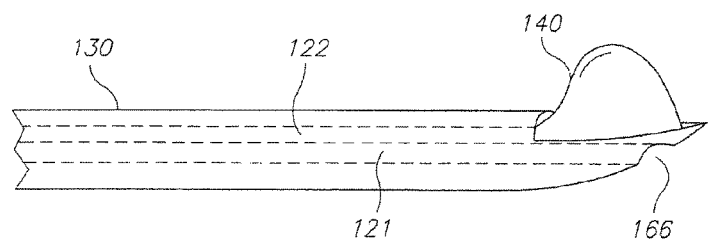

FIGS. 17F and 17G are high level schematic illustrations of needle 130 having opening 132 with length of between 2-4 mm through which balloon 140 may be expanded, according to some embodiments of the invention. Such needle 130 may be used directly to sense pressure applied by the surrounding tissue onto balloon 140, with or without use of cannula 110. In certain embodiments, a double lumen cannula 110 can be disposed inside needle 130, wherein a first lumen 121 facilitates a pathway of fluid, and wherein a second lumen 122 facilitates a pathway for insertion and evacuation of fluid into sensing balloon 140 located on distal end of cannula 110 (FIG. 17H). Sensing balloon 140 can only be inflated upwards and forward through opening 132. After detecting epidural space 70 using sensing balloon 140, needle 130 can be withdrawn. Then, a syringe or a catheter extension may be connected to cannula 110, for example using Luer lock connection 117, and a medication is administered into epidural space 70. In yet another embodiment, an additional opening 166 is positioned on tip 135 and is co-linear with the longitudinal axis of needle 130 (FIG. 17I). Opening 166 enables flow of fluid through lumen 121 and into the tissues, thus enabling the operator to perform LORT.

In certain embodiments, balloon 140 may be inflated to a small inner volume 122A during advancement of needle 130, small inner volume 122A selected to minimize distracting needle advancement while providing pressure measurements of surrounding pressure. Such a use may enable continuous pressure measurement during needle advancement, or at least repeated measurements during advancement, e.g. at a frequency of between 10-5000 Hz (measurements per second) during the actual advancement of needle 130 through the tissue.

Figure 19A:
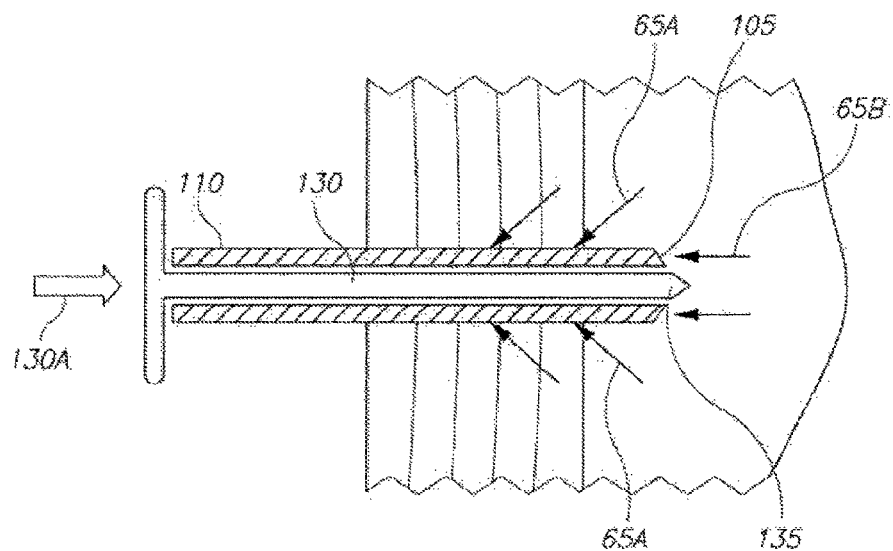
FIG. 19A-19B are high level schematic illustrations of lateral forces and frontal forces applied onto cannula
Figure 19B:
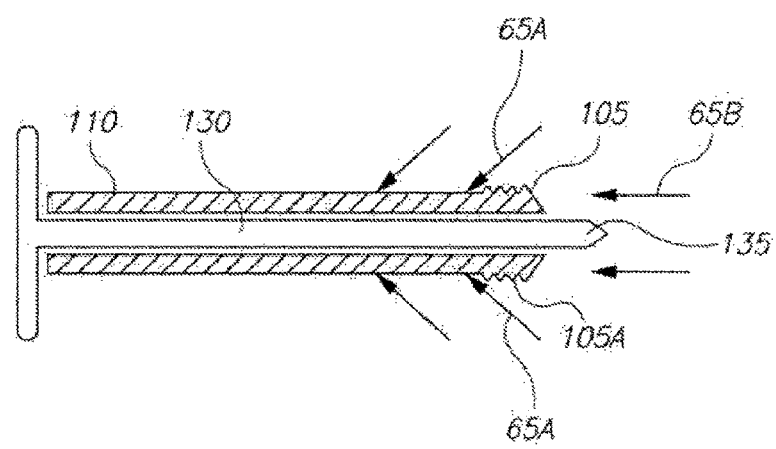
Figure 20A:
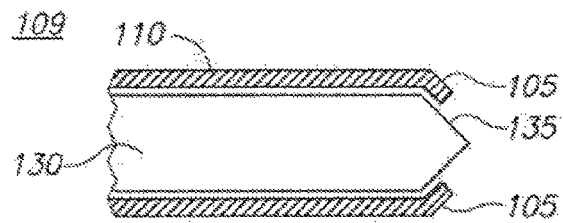
FIGS. 20A-20F are high level schematic illustrations of cannula tip stabilization configurations, according to some embodiments of the invention.
Figure 20B:
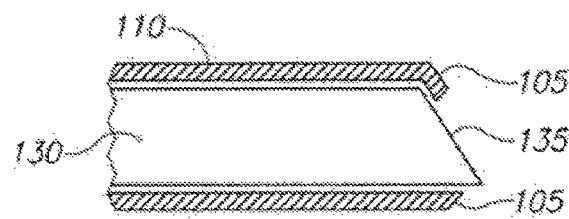
Figure 20C:
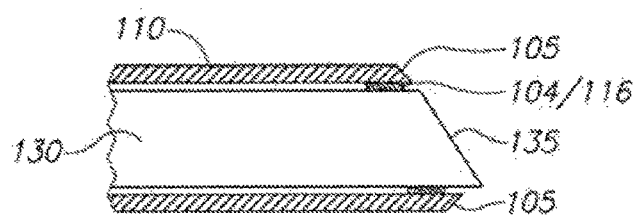
Figure 20D:
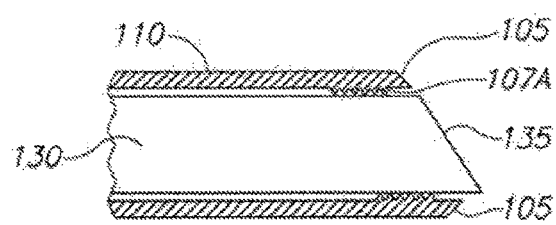
Figure 20E:
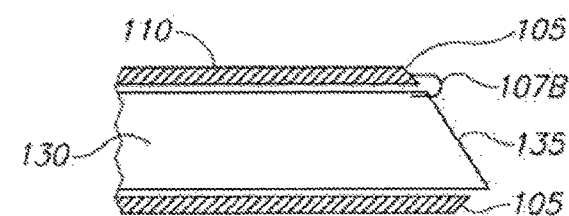

FIGS. 20A-20F are high level schematic illustrations of cannula tip stabilization configurations, according to some embodiments of the invention. FIGS. 19A and 19B schematically illustrate lateral forces 65A and frontal forces 65B applied onto cannula 110 upon advancement of needle 130 into tissue by an introduction force 130A. As illustrated in FIG. 19B, particularly frontal forces 65B may deform cannula tip 105 to slide backwards with respect to needle 130. FIGS. 20A-20F schematically illustrate various solutions to this condition and fixate a relative position of cannula and needle tips 105, 135 respectively, namely curving cannula tip 105 inwardly, along the whole perimeter of cannula tip 105 (FIG. 20A) or along a part thereof (FIG. 20B). In certain embodiments, cannula tip 105 may be curved inwardly to partly overlap needle tip 135. Narrowing cannula tip 105 protects cannula tip from being deformed or removed by frontal forces 65B. Sealing elements 104 may be introduced between cannula and needle tips 105, 135 respectively, to provide frictional attachment therebetween (FIG. 20C). In certain embodiments, sealing elements 104 may comprise sealing elements 116 (see above, FIGS. 5C, 5D). Cannula tip 105 may be configured to be coupled to needle tip 135 to maintain a distance between cannula tip 105 and needle tip 135 upon introduction of device 100 into tissue.

Figure 20F:
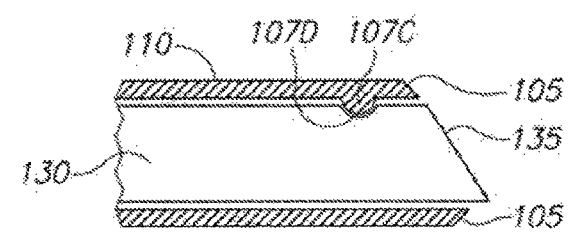

In certain embodiments, cannula tip 105 and needle tip 135 may be fully or partially attached to prevent a relative displacement between cannula tip 105 and needle tip 135. Such partial attachment may be achieved by roughening 107A cannula tip 105 internally (FIG. 20D) and/or roughening needle tip 135 externally, by directly connecting tips 105, 135 by a connecting member 107B (FIG. 20E, schematic, e.g., hook-like) or by forming a corresponding pair or pairs of protrusion(s) 107C and indentation(s) 107D in tips 105, 135 (FIG. 20F). Method 300 may further comprise coupling the cannula tip to the needle tip to maintain a distance between the cannula tip and the needle tip upon application of specified forced thereto, for example by curving the cannula tip inwardly to partly overlap the needle tip or by introducing a coupling element between the tips.

Figure 21A:
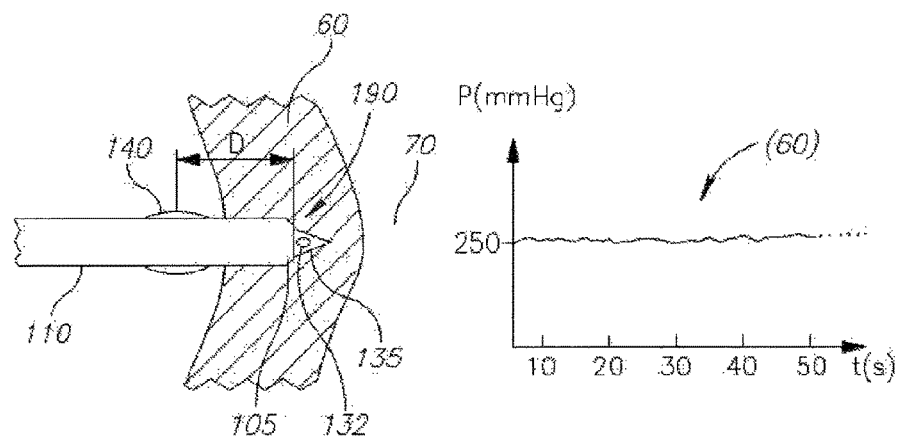
FIGS. 21A and 21B are high level schematic illustrations of quick and automatic restraining of needle advance upon its entry into the epidural space, according to some embodiments of the invention.
Figure 21B:
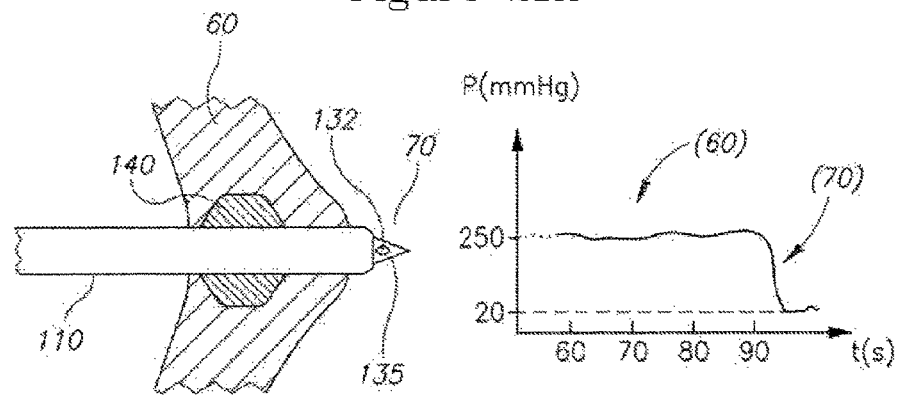

FIGS. 21A and 21B are high level schematic illustrations of quick and automatic restraining of needle advancement upon its entry into epidural space 70, according to some embodiments of the invention. Expandable element 140 such as balloon 140 may be located at a distance (D) of between 3-10 mm from distal end 190 of cannula 110. Contracted expandable element 140 (e.g., deflated balloon 140). Surrounding tissue pressure may be sensed by a sensing element as described above, or by the loss of resistance technique (LORT) through opening 132 in needle 130 (FIG. 21A). Upon detection of fallen pressure (note pressure fall in FIG. 21B, illustrating a non-limiting example of a pressure fall from 250 to 20 mmHg), which is possibly indicative of needle tip entry into epidural space 70, expandable element 140 may be expanded (e.g., balloon 140 inflated) immediately to prevent further advancement of needle 130, e.g., in ligamentum flavum tissue 60. System 150 may expand expandable element 140 upon detection of specified pressure falls or upon reaching specified pressure levels. If needed (e.g., in a case of false detection) expandable element 140 may be contracted (e.g., balloon 140 deflated) and needle advancement may proceed.

Figure 25A:
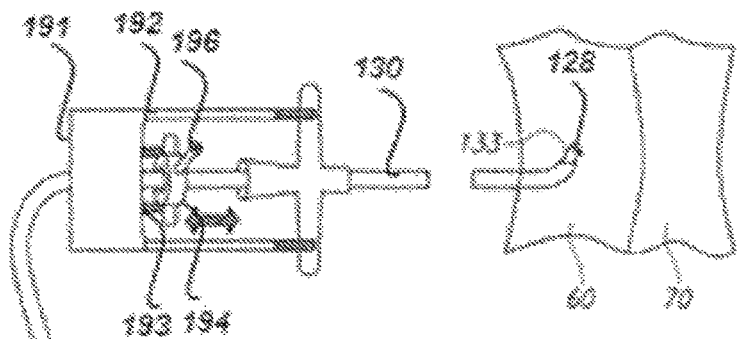
FIG. 25A-25C are high level schematic illustrations of using a stylet controlled by an actuator to safely enter the epidural space, according to some embodiments of the invention.

FIGS. 22A-22D are high level schematic illustrations of using stylet 133 to safely enter epidural space 70, according to some embodiments of the invention. Stylet 133 may be applied from within needle 130, e.g., pushed through needle inner lumen 124, or from within any sharp introducer such as a trocar, veress needle, Tuohy needle, pencil point needle, quincke needle, vascular cannulation or surgical tool. In certain embodiments, an actuator 191 (FIG. 25A) controls the advancement of stylet 133 by applying an appropriate force 133A. In certain embodiments, actuator 191 is fixated to needle, for example, fixation to wings 195 by two elongated rods 192. The linear moving shaft 193 of the actuator is attached to stylet 133 by locking mechanism 194. Locking mechanism 194 locks the moving shaft, for example, by a screw 196 that exerts force on stylet 133.

Figure 22E:
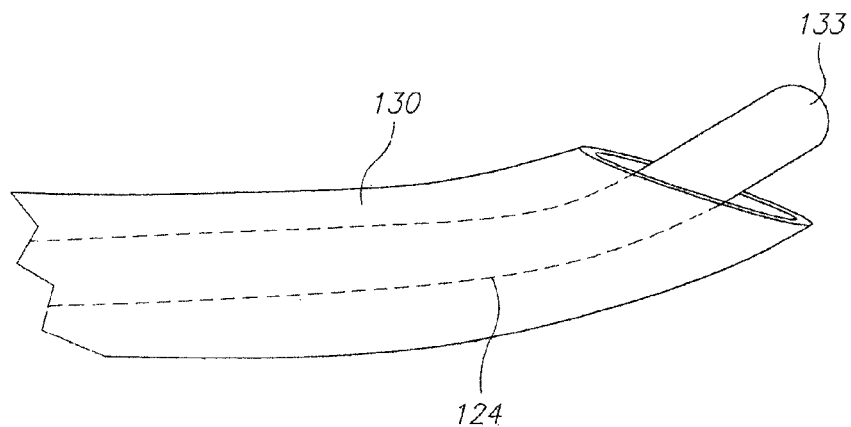
Figure 22F:
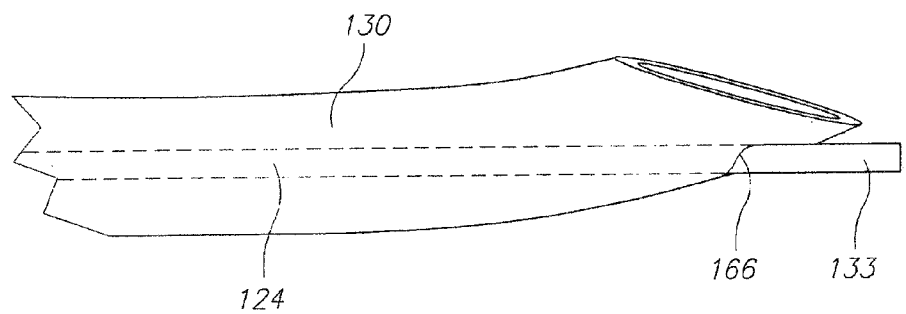

In certain embodiments the stylet can be pushed through a needle 130 having a curved tip, such as a Tuhoy needle (FIG. 22E), or through an additional opening 166 in the curved region of the needle (FIG. 22F).

In certain embodiments, stylet 133 may be advanced to push resilient tissue such as ligamentum flavum tissue 60 or other types of tissues. Stylet 133 may be blunt to allow measuring tissue resistance when tissue is being pushed to a certain distance (graphs in FIGS. 22A, 22B) without penetrating the tissue.

Stylet 133 may be repeatedly and controllably pushed forward (133A) ahead of needle 130 and then pulled back towards needle tip 135 to measure tissue resistance to manipulation. The push-pull movement may be performed when needle 130 is static or as it advances. The push-pull movement may also be continuous along the penetration through different tissues, or may be event-driven, for example, by a decision of the operator or by reaching a certain force threshold. Actuator 191 may advance stylet with constant velocity and pull it backwards with the same velocity or with a different velocity. For example, pushing velocity can be 1-5 mm per second, while pulling velocity can be 5-20 mm per second. Needle 130 may be used by itself or from within any embodiment of cannula 110 described above. For example, stylet 133 may controllably traverse a distance of between 1-5 mm at a constant velocity, and a controlling system may measure the force applied on stylet tip by tissue as a function of the traversed distance. The measurements may be used to indicate tissue type and deformation and may be used to monitor the advancement of needle 130. For example, the measurements may be compared to known tissue responses (e.g., of ligamentum flavum 60). Controlling system (not shown) may comprise a sensor (for instance, a load cell). One advantage of such a force measurement is measuring only the forces applied on the tip of stylet 133 by adjacent tissue.

The measurement could be also sent to a microprocessor 153 to further analyze the data with mathematical tools for example to calculate the work required by the stylet 133 to push the tissue.

In yet another embodiment, the controlling system maintain preconfigured force applied on stylet 133, by pushing stylet 133 further ahead of needle 130 when measured force drops below the preconfigured force, or by pulling stylet 133 backwards towards needle tip 135 when measured force exceeds the preconfigured force. By further analyzing stylet traversed distances, the type of tissue engaged with stylet 133 can be determined.

Stylet 133 can also be advantageous in detecting bony structures ahead of needle 130. When needle 130 is facing a bony structure, a measurement of force applied on stylet 133 during a pushing movement will be very big, thus indicating the existence of a bony structure ahead of needle 130. In an epidural injection, for example, such indication will assist the operator in changing the path of needle 130 before heating a bony structure that can harm the needle tip and risk the entire procedure.

Figure 24A:
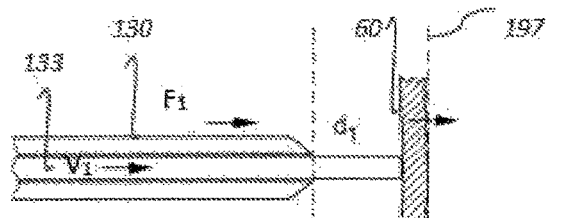
FIGS. 24A-24D are high level schematic illustrations of an exemplary method of penetrating an elastic tissue with minimum overshoot using a stylet, according to some embodiments of the invention.
Figure 24B:
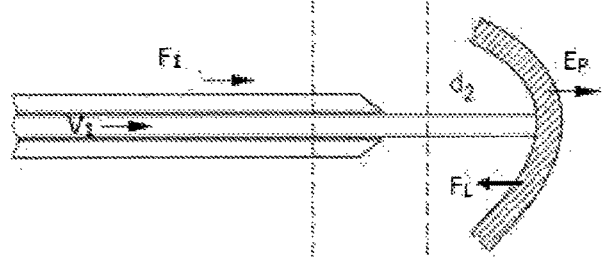
Figure 24C:
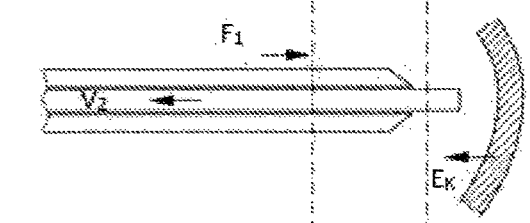
Figure 24D:
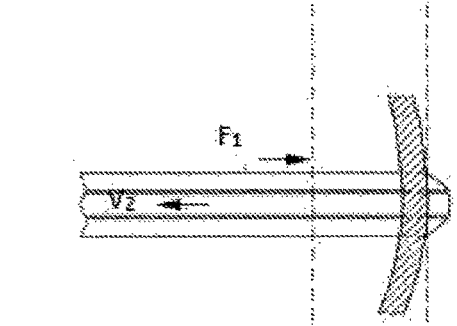

Furthermore, stylet 133 can reduce the overshoot of needle 130 while penetrating into a body cavity (such as the epidural space) through an elastic tissue. FIG. 24 is a high level schematic illustration showing how stylet 133 reduces the needle overshoot. For example, during a needle insertion into ligamentum flavum 60 and towards epidural space 70, needle 130 is advanced forward at force $F_1$ while stylet 133 is being pushed forward in a controlled manner by actuator 191 at a constant velocity $V_1$ to a distance $d_1$ beyond tip 135 (FIG. 24A). Actuator 191 continues to push forward stylet 133 at constant velocity $V_1$ to a distance $d_2$ ($d_2 > d_1$) and thus deflects ligamentum flavum 60 from its resting position 197 to a tented position, where ligamentum flavum 60 accumulates potential energy $E_P$ and apply Force $F_L$ on stylet 133. Stylet 133 does not cross ligamentum flavum into epidural space 70 due to its blunt tip (FIG. 24B). A fast retraction of stylet 133 backwards by actuator 191 at velocity $V_2$ enables the deflected tissue to convert its potential energy $E_p$ to kinetic energy $E_k$ as tissue rapidly return to its rest position 197 while penetrating through needle 130 that is advancing forwards with minimum overshoot of ligamentum flavum 60 (FIGS. 24C-24D).

In one embodiment, the pushing movement of Stylet 133 ahead of needle tip 135 while needle 130 is being advanced by the operator in dense tissues, increases the tactile feedback that the operator encounters. This increase is achieved since the force $F_L$ applied on stylet 133 is added to the force that is applied on needle 130 when actuator 191 is fixated to needle 130. Thus, differentiation between dense tissues and complaint tissue is increased.

Furthermore, stylet 133 protects the needles inner lumen 124 from being filled by tissue debris and fluids.

Figure 22G:
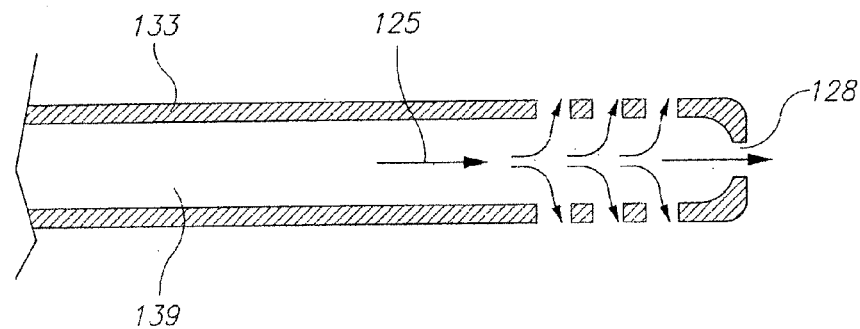

In certain embodiments (FIGS. 22C and 22D), stylet 133 may comprise an internal stylet lumen 139 for delivering fluid 125 to carry out the loss of resistance technique (LORT) through an opening 128 at the end of stylet 133. In another embodiment, stylet 133 may comprise several lateral orifices to deliver fluid 125 in several directions (FIG. 22G). Such measurement provides epidural space identification prior to needle penetration.

In another embodiment, stylet 133 may be used to perform the penetration into epidural space 70 ahead of needle 130. Such an embodiment is beneficiary since stylet 133 smaller outer diameter and blunt tip will reduce the tissue trauma during penetration in comparison to a standard needle, such as a Tuohy needle with an outer diameter of 1.3-1.6 mm. Even in case stylet 133 penetrates dura mater 80, the damage is much smaller than done by a penetration of needle 130. In certain non-limiting embodiments, stylet 133 may have a diameter of $S_1=0.8$-$0.9$ mm (see FIG. 22D) and internal stylet lumen 139 may have a diameter of $S_2=0.5$-$0.7$ mm. Stylet 133 may be made of any biocompatible material known in the art, such as different kinds of plastic, nylon, stainless steel or Nitinol.

Stylet 133 may be configured to receive its pushing strength from surrounding needle, and be flexible upon extending over a certain threshold beyond needle 130, thus adding another safety layer in preventing dangerous overshooting during penetration. For example, stylet 133 may be configured to become flexible when extending, for example, 4 mm ahead of needle tip 135, so that when needle 130 is static and stylet 133 is being pushed forward, maximum overshoot will not exceed 4 mm. In certain embodiments (FIG. 22D) stylet 133 may be strengthened by a supportive member 138 such as a ring or a reinforcing spring.

Figure 25B:
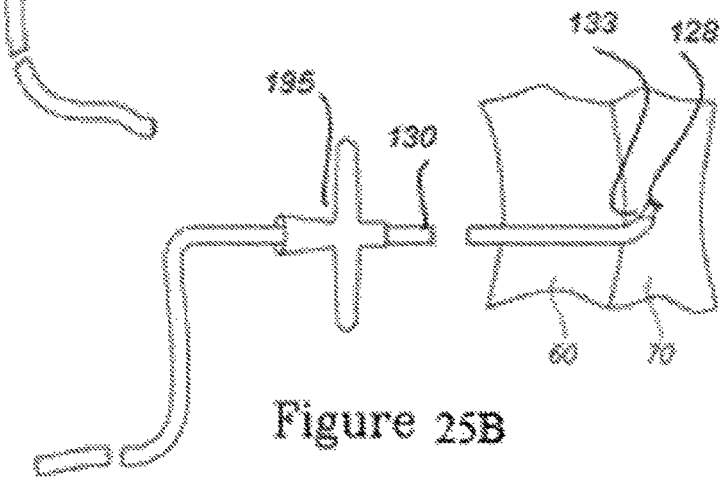
Figure 25C:
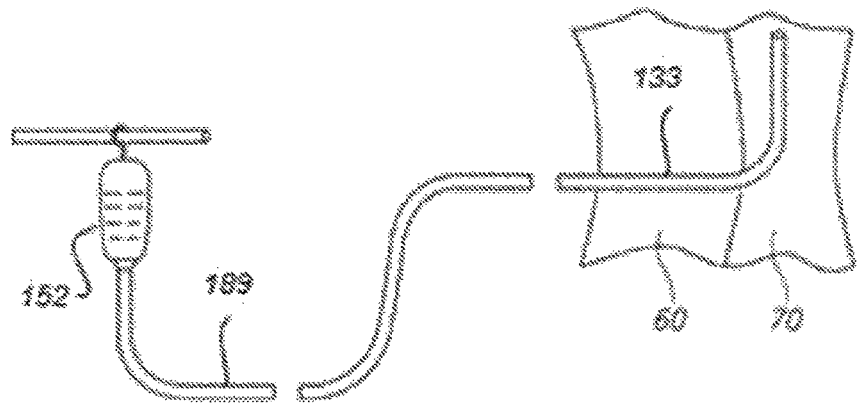

In certain embodiments, stylet 133 may be configured as a catheter (e.g., controllable via a Luer fitting) that may be advanced as described into epidural space 70 and then be left there after removal of needle 130 (in case stylet strength is provided by needle 130, needle removal leaves stylet 133 as flexible catheter 133 in the epidural space). In one embodiment, after detection of epidural space 70 locking mechanism 194 of stylet 133 is unscrewed and actuator 191 connected to the wings 195 is detached and slides backwards, leaving stylet 133 and needle 130 inside epidural space 70 (FIG. 25B). Then, needle 130 is removed, and stylet 133 is connected to extension tube 189 and can be used as a catheter for administered substances into epidural space 70 (FIG. 25C). In another embodiment, upon detection of epidural space 70, stylet 133 is removed and a medication is administered either directly through needle 130 using a syringe, or through an epidural catheter that is threaded through needle 130.

Figure 23:
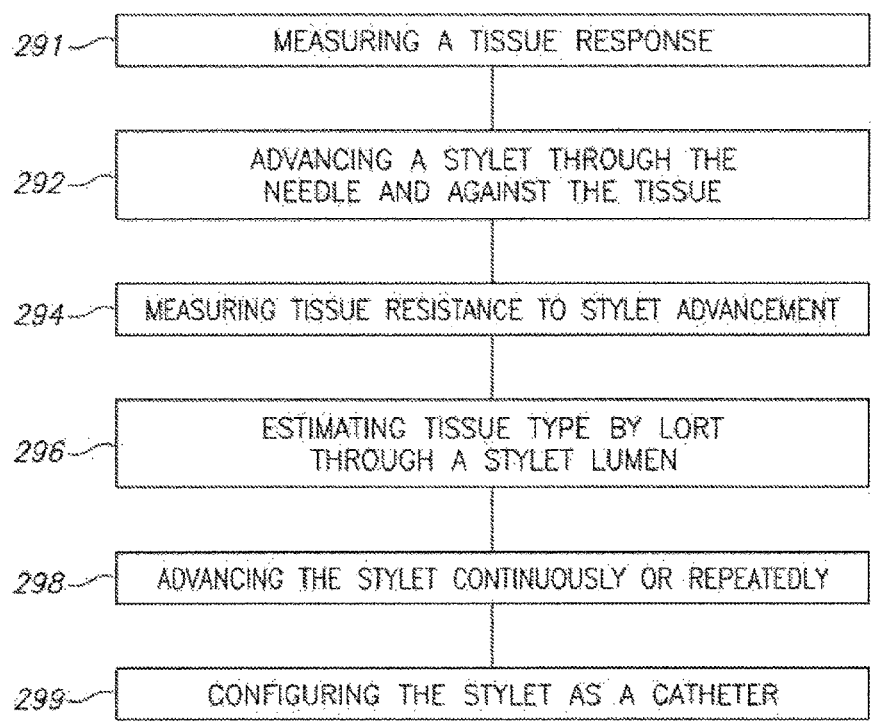
FIG. 23 is a high level schematic flowchart illustrating a tissue sensing method, according to some embodiments of the invention.

FIG. 23 is a high level schematic flowchart illustrating a tissue sensing method 290, according to some embodiments of the invention. Method 290 may comprise measuring a tissue response (stage 291) by advancing a stylet through the needle and against the tissue (stage 292) and measuring tissue resistance to stylet advancement (stage 294). In certain embodiments, the stylet may comprise an internal stylet lumen used to estimate tissue type by LORT (stage 296). In certain embodiments, the stylet may be advanced continuously or repeatedly (stage 298). In certain embodiments, the stylet may be configured as a catheter (stage 299).

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. An apparatus for safely positioning an introducer or a stylet inside a mammalian tissue, the apparatus comprising:
   a hollow introducer having a longitudinal axis and a distal end;
   a stylet movable through the hollow introducer and arranged to be controllably pushed out of the distal end of the introducer and against the mammalian tissue;
   an actuator arranged to controllably push the stylet out of the distal end of the introducer or pull it back towards the distal end;
   a sensor arranged to measure a force or a pressure required to push the stylet against the mammalian tissue; and a processor arranged to record and analyze the measurements and determine therefrom a type of the mammalian tissue and transitions between different mammalian tissues and cavities.

2. The apparatus of claim 1, wherein the stylet comprises an inner lumen and at least one distal orifice arranged to introduce fluid into the tissue to sense tissue pressure.

3. The apparatus of claim 1, wherein the stylet is configured to receive its pushing strength from surrounding introducer, and be flexible upon extending over a certain threshold beyond introducer.

4. The apparatus of claim 2, wherein the stylet is arranged to be usable as a catheter after withdrawal of the introducer.

5. The apparatus of claim 1, wherein the introducer comprises any of: a thin needle, a Veress needle, an epidural needle, a biopsy needle, a trocar, a cannula, a catheter, a Tuohy type needle, a spinal needle, a pencil point needle, a guidewire, a surgical instrument and a sharp tool.

6. The apparatus of claim 1, wherein the stylet is arranged to perform a push-pull movement to measure the force applied on the stylet by the mammalian tissue per the displacement of the mammalian tissue in order to facilitate determining the type of tissue by the processor.

7. The apparatus of claim 1, wherein the stylet has a blunt tip arranged to enable a pushing action without cutting of mammalian tissue.

8. The apparatus of claim 1, wherein the stylet is arranged to penetrate a tissue ahead of the introducer.

9. A method of detecting the type of a mammalian tissue, comprising:
   inserting into a mammalian tissue a hollow introducer having a distal tip, the introducer having a stylet moveable therethrough;
   controllably pushing the stylet through the distal tip of the introducer and against a mammalian tissue using an actuator;
   measuring the force applied against the stylet per displacement using a sensor;
   analyzing the measurement using a processor to facilitate determining a type of the mammalian tissue and a transition between tissues and cavities.

10. The method of claim 9, further comprising repeatedly pushing the stylet against the mammalian tissue to a predefined distance and pulling the stylet back rapidly to enable continuous insertion of the introducer.

* * * * *